United States Patent
Ryan et al.

(10) Patent No.: US 7,066,954 B2
(45) Date of Patent: Jun. 27, 2006

(54) ANNULOPLASTY SYSTEM

(75) Inventors: Timothy R Ryan, Shorewood, MN (US); Joseph C. Morrow, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/792,631

(22) Filed: Mar. 3, 2004

(65) Prior Publication Data

US 2004/0186564 A1    Sep. 23, 2004

Related U.S. Application Data

(62) Division of application No. 10/100,444, filed on Mar. 18, 2002, now Pat. No. 6,719,786.

(51) Int. Cl.
*A61F 2/24* (2006.01)
(52) U.S. Cl. ............................ 623/2.36; 623/2.11
(58) Field of Classification Search ............... 623/2.11, 623/2.36, 2.37
See application file for complete search history.

(56) References Cited

U.S. PATENT DOCUMENTS

| | | | |
|---|---|---|---|
| 3,656,185 A | 4/1972 | Carpentier | |
| 3,828,787 A | 8/1974 | Anderson et al. | |
| 4,042,979 A | 8/1977 | Angell | |
| 4,055,861 A | 11/1977 | Carpentier et al. | |
| 4,106,129 A | 8/1978 | Carpentier et al. | |
| 4,185,636 A | 1/1980 | Gabbay | |
| 4,204,283 A | 5/1980 | Bellhouse et al. | |
| 4,290,151 A | 9/1981 | Massana | |
| 4,306,319 A | 12/1981 | Kaster | |
| 4,535,483 A | 8/1985 | Klawitter | |
| 4,612,011 A | 9/1986 | Kaultzky | |
| 4,743,253 A | 5/1988 | Magladry | |
| 4,755,181 A | 7/1988 | Igoe | |
| 4,865,600 A | 9/1989 | Carpentier et al. | |
| 4,911,164 A | 3/1990 | Roth | |
| 4,932,965 A | 6/1990 | Phillips | |
| 5,011,481 A | 4/1991 | Myers et al. | 606/1 |
| 5,104,407 A | 4/1992 | Lam et al. | 623/2 |
| 5,350,420 A | 9/1994 | Cosgrove et al. | 623/2 |
| 5,415,667 A | 5/1995 | Frater | |
| 5,522,884 A | 6/1996 | Wright | 623/2 |
| 5,669,919 A * | 9/1997 | Sanders et al. | 606/148 |
| 5,871,489 A * | 2/1999 | Ovil | 606/148 |
| 5,984,959 A * | 11/1999 | Robertson et al. | 623/2.11 |
| 6,183,512 B1 | 2/2001 | Howanec, Jr. et al. | 623/2.36 |
| 6,283,993 B1 | 9/2001 | Cosgrove et al. | 623/2.11 |
| 6,319,280 B1 * | 11/2001 | Schoon | 623/2.11 |
| 6,332,893 B1 | 12/2001 | Mortier et al. | 623/2.36 |

(Continued)

FOREIGN PATENT DOCUMENTS

AU    464075    5/1973

(Continued)

OTHER PUBLICATIONS

Surgical Techniques for the Repair of Anterior Mitral Leaflet Prolapse / Carlos M.G. Duran, M.D., Ph.D. / J Card Surg 1999; 14:471-481.

(Continued)

*Primary Examiner*—Corrine McDermott
*Assistant Examiner*—Thomas J. Sweet
(74) *Attorney, Agent, or Firm*—Tom Berry; Jeffrey J. Hohenshell

(57) ABSTRACT

An annuloplasty system including an annuloplasty prosthesis and a holder for the prosthesis.

19 Claims, 17 Drawing Sheets

U.S. PATENT DOCUMENTS

| | | | |
|---|---|---|---|
| 6,406,492 B1 | 6/2002 | Lytle | |
| 6,409,758 B1 | 6/2002 | Stobie et al. | |
| 6,702,852 B1 | 3/2004 | Stobie et al. | |
| 6,719,786 B1 | 4/2004 | Ryan et al. | |
| 6,786,924 B1 | 9/2004 | Ryan et al. | |
| 6,955,689 B1 | 10/2005 | Ryan et al. | |
| 2001/0049558 A1* | 12/2001 | Liddicoat et al. | 623/2.36 |
| 2003/0176917 A1 | 9/2003 | Ryan et al. | |
| 2004/0024451 A1 | 2/2004 | Johnson et al. | |
| 2005/0197696 A1 | 9/2005 | Duran | |

FOREIGN PATENT DOCUMENTS

| | | |
|---|---|---|
| GB | 2083362 | 2/1982 |
| GB | 2108393 | 5/1983 |
| WO | WO 00/59408 | 10/2000 |

OTHER PUBLICATIONS

Medtronic Booklet "Medtronic Duran Flexible Annuloplasty Systems In-Service Guide" / UC200004685 EN.

Carpentier-Edwards Physio Annuloplasty Ring, "Technical Product Manual," Baxter (1996) (22 pages).

Ian J. Reece, M.B., F.R.C.S., et al., "Surgical Treatment of Mitral Systolic Click Syndrome: Results in 37 Patients," The Annals of Thoracic Surgery, vol. 39, No. 2, Feb. 1985 (pp. 155-158).

Denton A. Cooley, M.D., et al., "Mitral Leaflet Prolapse: Surgical Treatment Using a Posterior Annular Collar Prosthesis," Cardiovascular Diseases, Bulletin of the Texas Heart Institute, vol. 3, Nov. 4, 1976 (pp. 438-439; 442-443).

* cited by examiner

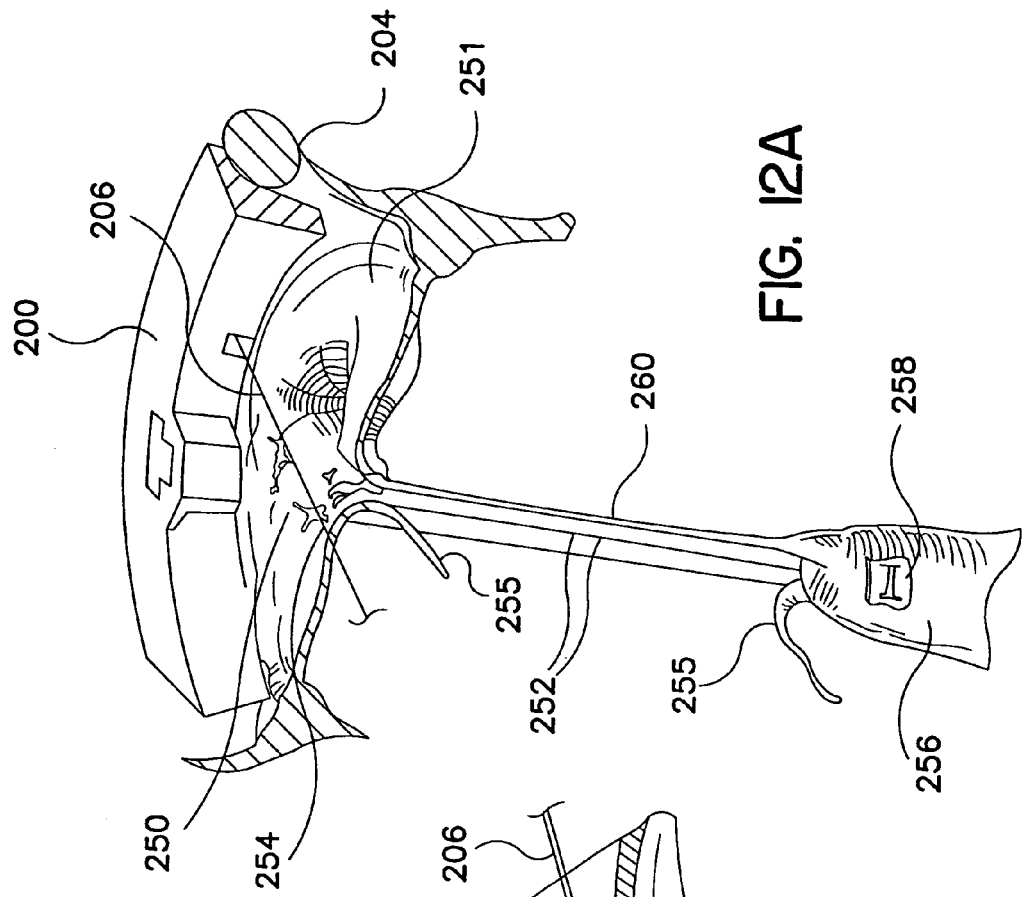
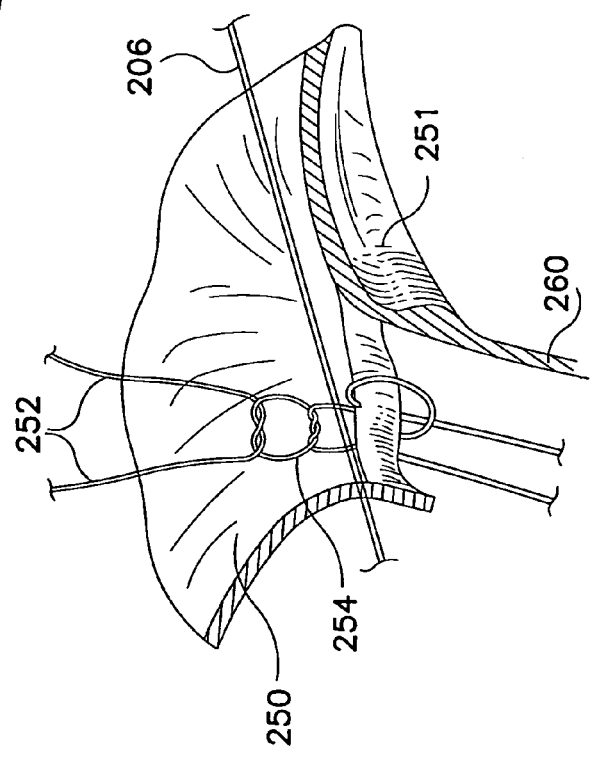
FIG. 12A
FIG. 12B

ANNULOPLASTY SYSTEM

CROSS-REFERENCE TO RELATED APPLICATIONS

This application is a divisional application of U.S. Ser. No. 10/100,444 filed Mar. 18, 2002 titled FLEXIBLE ANNULOPLASTY PROSTHESIS AND HOLDER now U.S. Pat. No. 6,719,786.

BACKGROUND OF THE INVENTION

The present invention relates generally to surgical tools and more particularly for surgical tools used in conjunction with prostheses such as annuloplasty rings and bands.

Annuloplasty rings and bands are useful in a variety of surgical procedures, including mitral and tricuspid annular reduction. In these procedures, sutures are first placed around all or portions of the valve annulus at spaced intervals. Sutures passing through the annulus in regions in which reduction of the valve annulus is desired are spaced equidistant from one another, for example, at 4 mm intervals. These sutures are then brought through the annuloplasty ring or band more closely spaced than where they pass through the annulus, for example, 2 mm. The process of passing the sutures through the ring or band occurs while the prosthesis is held above the valve annulus. The ring is then moved down into contact with the valve annulus, causing contraction of the annulus, thus effecting a reduction in valve annulus circumference. This basic procedure is used to correct both mitral and tricuspid annular dilatation.

In order for the sutures to be passed through the annuloplasty ring, it is desirable that the ring be held in a fixture or tool of some fashion. One early tool was manufactured by Pilling Instruments, and took the general form of a cone provided with a circumferential groove near the base. The cone was also provided with longitudinal slits, so that the tool could be contracted to accept the ring around the circumference of the groove. The tool was adapted to be held by means of a threaded handle.

More recent holder designs are disclosed in U.S. Pat. No. 6,283,993, wherein sutures passing through the prosthesis are used to retain it in a circumferential groove on the holder. An alternative design is disclosed in U.S. Pat. No. 5,011,481, which employs radially and downwardly extending fingers in conjunction with sutures passing around the prosthesis to retain it on the holder. Yet another alternative design is disclosed in U.S. Pat. No. 5,522,884, in which an adjustable annuloplasty ring is retained on its holder by tightening the adjusting sutures within the ring to contract it into a circumferential groove on the holder.

Examples of flexible annuloplasty bands and rings are also disclosed in the above cited patents, all of which are incorporated herein by reference in their entireties.

SUMMARY OF THE INVENTION

The present invention is directed toward an improved holder for use with annuloplasty prostheses. The holder is specifically configured to assist the surgeon in performing the technique of mitral or tricuspid reduction, and is typically provided in conjunction with the annuloplasty ring or band, ready for use. The holder takes the general form of an oblate ring component having an upper surface, a lower surface and an outer circumferential surface corresponding generally to the configuration of a valve annulus. The prosthesis extends around at least a portion of this circumferential surface and is releasably retained alongside this surface during the passing of sutures through the prosthesis.

The present invention provides improvements directed to the mechanism for retaining the prosthesis on the holder during passage of the sutures and releasing the prosthesis after positioning on the valve annulus. In some embodiments, rather than retaining the annuloplasty ring to the holder by means of sutures passing through the annuloplasty ring, the ring is retained by means of downwardly extending penetrating members such as barbs, pins, pegs, or needles, which enter the annuloplasty prosthesis and retain it to the holder during passage of sutures through the prosthesis. These penetrating members may be fabricated of metal or molded plastic and are sufficiently rigid that they are not readily deflected outward to allow outward movement of the annuloplasty prosthesis away from the holder. The penetrating members may have sharpened or relatively blunt tips.

Some of the preferred embodiments employ a two-component holder in which the first component includes the circumferential surface around which the prosthesis is mounted and the second component carries the penetrating members. In these embodiments, the first component also typically includes radially extending projections that prevent the prosthesis from moving downward off of the penetrating members, until upward movement of the second component. In some of these embodiments, the first and second holder components are retained to one another, and in others, they are removable from one another. In some embodiments, the first and second holder components are retained adjacent to one another during passage of sutures through the prosthesis by means of a suture or sutures coupling the first and second components together. In these embodiments, the first and second components become movable relative to one another following cutting of the suture or sutures retaining them together. In other embodiments, a suture is employed in order to maintain the annuloplasty prosthesis on the holder, but release of the prosthesis is simplified by the provision of a cutting mechanism, integrated into the structure of the holder itself. The first and second holder components are preferably molded of generally rigid plastics but might in some cases be fabricated of metal or other materials.

The embodiments of the present invention generally are intended to provide a simplified and more easily employed mechanism for holding the annuloplasty prosthesis during passage of the sutures through the prosthesis and for releasing it from the holder after the ring has been moved downward into its intended location on the valves annulus.

BRIEF DESCRIPTION OF THE DRAWINGS

FIGS. 12A and 12B are cut-away views illustrating the use of the holder of FIG. 7 in conjunction with a surgical repair procedure.

DETAILED DESCRIPTION OF THE PREFERRED EMBODIMENTS

Figure 1:
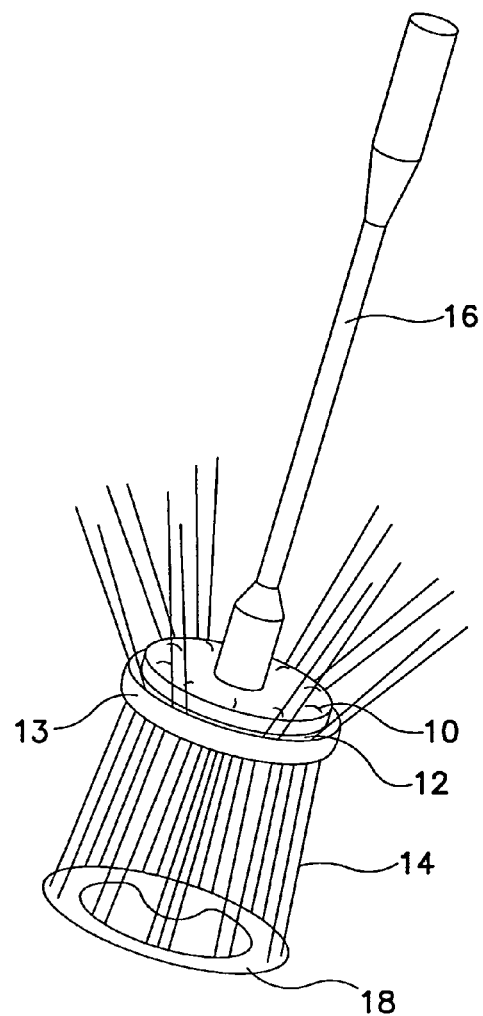
FIG. 1 illustrates a prior art annuloplasty prosthesis and holder, after passage of sutures through the annuloplasty prosthesis.

FIG. 1 is a perspective view of a two-piece annuloplasty holder according to the prior art. In particular, the holder system as illustrated is described in the brochure "Medtronic Duran Flexible Annuloplasty Systems In Service Guide", published by Medtronic, Inc. in 2000, Publication No. UC200004685 EN, incorporated herein by reference in its entirety. The holder system includes a handle 16 which may be made of metal or plastic, and which may, in some embodiments, include a malleable shaft allowing for manual reconfiguration of the shaft. The shaft is snapped into the holder itself, which includes two components 10 and 12 which are molded of rigid plastic. The upper component 10 of the holder is transparent and serves as a template, including markings illustrating the locations of the valve trigones and regularly spaced markings assisting in placement of sutures around the annuloplasty prosthesis 13. As illustrated, the first component 12 of the prosthesis releasably secured to the second component 10 of the prosthesis and the annuloplasty prosthesis 13 is mounted around a circumferential surface of the first holder component 12.

As illustrated sutures 14 have been passed through the valve annulus 18 and upwardly and outwardly through the prosthesis 13 itself, according to conventional practice for implantation of annuloplasty prostheses. The holder system is then used to move the prosthesis 13 downwardly along the sutures so that it is seated adjacent to the upper surface of the annulus 18. The second component 10 of the holder may be removed from the first component 12 by cutting the sutures holding them together, leaving the ring mounted around the first holder component 12, seated adjacent the valve annulus. Although not visible in this view, the first component 12 of the holder includes a large central orifice, so that testing to assure that leaflets of the heart valve co-apt can be accomplished while the prosthesis 13 remains on the first component 12 of the holder. In the particular product marketed by Medtronic, Inc., removable of the prosthesis 13 from the first holder component 12 was accomplished by cutting sutures that held the prosthesis on the holder.

Figure 2:
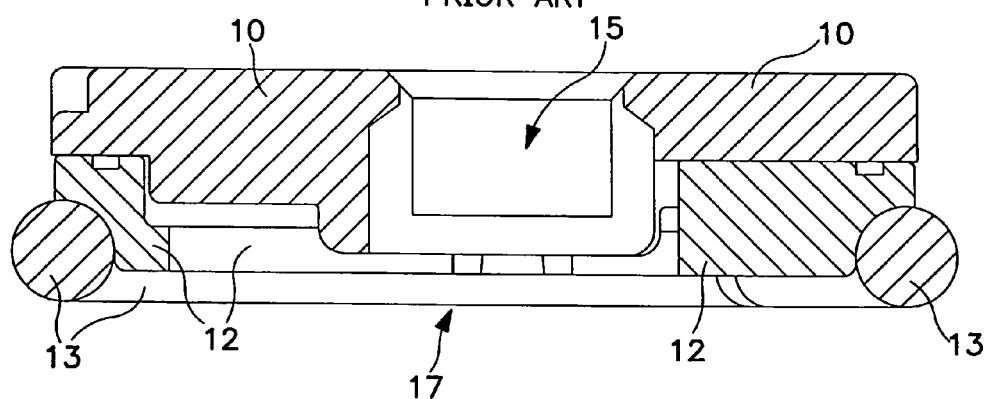
FIG. 2 illustrates a cross section through a prior art annuloplasty prosthesis holder.

FIG. 2 is a cross section through the first and second components of the holder illustrated in FIG. 1, in conjunction with attached annuloplasty prosthesis 13. In this view it can be seen that the second component 10 of the holder is provided with a formed recess 15 configured to releasably engage a handle 16 (FIG. 1). In this view also it can be seen that the first holder component 12 defines a large central aperture illustrated generally at 17, through which operation of the associated heart valve can be observed after removal of the second holder component 10. As noted above, component 10 is held to component 12 by means of cuttable sutures, and prosthesis 13 is likewise maintained mounted to component 12 by means of cuttable sutures. Mounting of the prosthesis 12 to the first component 12 of the holder by means of these sutures requires handwork, increasing the expense and complexity of production of the system comprising the holder and the prosthesis. In addition, release of the prosthesis 13 from the first holder 12 requires multiple cuts of the sutures holding the prosthesis to the first holder component 12, complicating the procedure for releasing the prosthesis from the holder.

Figure 3:
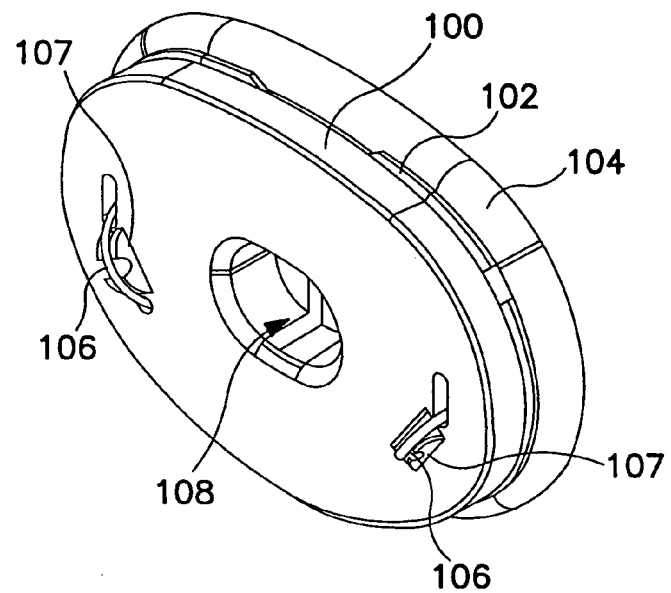
FIG. 3 illustrates a perspective view from above of a two-component annuloplasty prosthesis holder, according to a first embodiment of the invention.

FIG. 3 is a perspective view from the upper surface of a two-component annuloplasty valve holder according to a first embodiment of the present invention. The holder includes a first component 102, around which the annuloplasty prosthesis 104 is mounted and a second component 100, releasably secured to the first component by means of sutures 106. Sutures 106 pass through both the first and second components of the holder and, upon cutting at slots 107, release the first and second components from one another. The second component also includes a formed recess 108 corresponding to that illustrated in FIG. 2, for releasably receiving a handle, which may correspond to handle 16, illustrated in FIG. 1. As is the case for the alternative embodiments discussed below, recess 108 may be replaced by a snap fitting, a threaded bore, or other mechanism for connecting to a handle.

Figure 4:
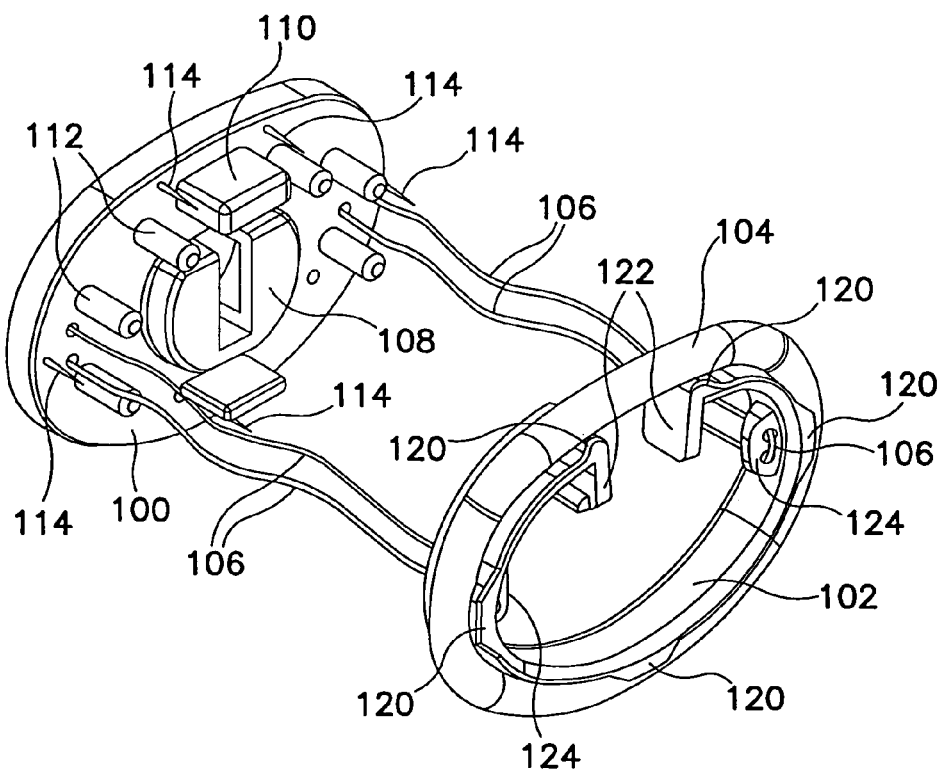
FIG. 4 is a perspective view of the two components of the embodiment of FIG. 3 wherein the first and second components are separated from one another.

FIG. 4 illustrates the components of the holder of FIG. 3 spaced from one another, as seen from below the two components. In this view it can be seen that the second component 100 of the holder is provided with a series of projecting barbs or pins, 114 extending at spaced locations around component 100. In use, these barbs or pins penetrate into the prosthesis 104 and comprise part of the mechanism for retaining the holder 104 on the holder. Projections 112, also located around the ring are provided to assist alignment of the first holder component 102 on the second holder component. A rectangular projection 110 is provided in order to prevent deformation of the first holder component as described below. Sutures 106 are illustrated schematically, illustrating the path that they follow, extending through holes formed in the second component 100 and in tabs 124, formed in the first component. In use, of course, the sutures are tightened to hold the components adjacent to one another, and ends of the sutures are anchored in the upper component 100.

The first component 102 of the holder generally takes the form of an open ring, having a circumferential surface around which the annuloplasty prosthesis 104 is mounted. The open ring is provided with radially outwardly extending projections 120, located adjacent and extending along the lower surface of the prosthesis 104. As illustrated, these projections are at locations corresponding to the locations of pins 114, and served to prevent downward movement of the prosthesis 104, off of pins 114. The ends of the open ring defined by the first holder component 102 are provided with inwardly extending projections 122 which may be grasped by a forceps or hemostat. These projections when moved toward one another decrease the circumference of the holder component 102 and facilitate removal of the prosthesis 104 over projections 120.

In use, the prosthesis 104 is mounted to the first component 102 and the first component is secured adjacent the second component 100 by means of sutures 106.

In this configuration, pins 114 pass through the prosthesis 104, in regions above the projections 120, so that the prosthesis 104 cannot be moved downwardly off of the pins 114. In addition, rectangular projection 110 is located between inwardly directed projections 122 of the first holder component 102, preventing movement of projections 122 toward one another and preventing corresponding reduction of the circumference of the first component 102.

During the surgical procedure, sutures as illustrated in FIG. 1 are passed upwardly from the valve annulus through the prosthesis 102 while the first and second components 100, 102 of the holder are located adjacent one another, retaining the prosthesis 104 on the holder. After the annuloplasty prosthesis 104 is slid downwardly along the sutures and placed adjacent the heart valve annulus, sutures 106 connecting the first and second components 102, 100 of the holder are cut, allowing for upward movement of the second holder component 100 away from the first holder component 102. Upward movement of the second holder component results in removal of pins 114 from the prosthesis 104 and removal of rectangular projection 110 from between the inwardly extending projections 122 of first component 102. The surgeon may then squeeze projections 122 with a forceps or hemostat, moving them toward one another reducing the outer circumference of the first component 102, further facilitating removal of the prosthesis 104 over projections 120.

Figure 5:
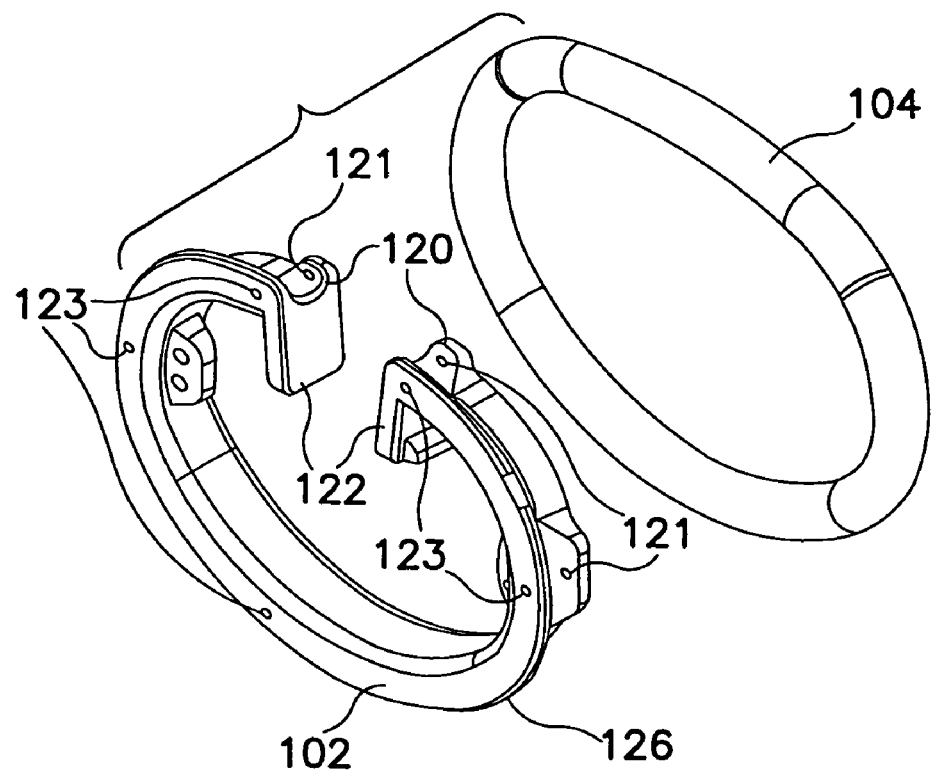
FIG. 5 is a perspective view of the first component of the embodiment of FIG. 3, with the annuloplasty prosthesis removed.

FIG. 5 illustrates the first component 100 of the holder, with the annuloplasty prosthesis 104 removed. In this view it can be seen that the first component of the holder includes a circumferential radially projecting flange 126, which lies along the upper surface of the annuloplasty prosthesis 104, when mounted to the first component 100. In addition, it can be seen that the radially extending flange 126 is provided with a series of holes 123 through which pins 114 pass, and that likewise, in this particular embodiment, the radially extending projections 120, located adjacent to the lower edge of the prosthesis when mounted to component 100 also are provided with holes 121 to receive the lower extremities of pins 114.

Figure 6:
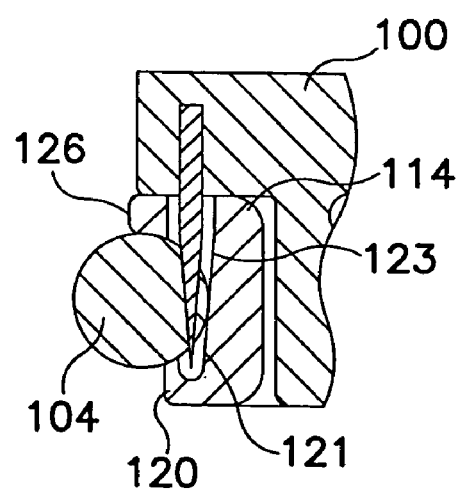
FIG. 6 is a cross sectional view through a portion of the embodiment of FIG. 3.

The structural interrelation of the first and second components and the prosthesis is illustrated in more detail in FIG. 6 which is a cross sectional view through a portion of components 100 and 102, with prosthesis 104 attached. In this view it can be seen that when the first component 102 of the holder is located adjacent to the second component 100, pin 114 passes downward through holes 123 in the upper, radially extending flange 126 of component 102 through the prosthesis 104 and into holes 121 in the radially extending projection 120s, extending adjacent the lower surface of the annuloplasty prosthesis 104. This mechanical interlock prevents removal of the prosthesis from the holder. Upward movement of the second holder component 100 relative to the first component 102 causes withdrawal of pin 114, allowing for subsequent release of the annuloplasty prosthesis 104.

In the specific embodiment illustrated, pins 114 extend all the way through the prosthesis 104 and into corresponding recesses 121 in the lower, radially extending projections 120. In other embodiments, pins 114 may be shortened and need not extend all the way to or into the lower radially extending projections 120. Extension of the pins 114 to or preferably into the projections 120 may be especially desirable if the annuloplasty prosthesis 104 is very flexible and or extensible, such as in the case of the Duran TM prosthesis as illustrated in the Medtronic brochure cited above. This feature may be less beneficial if the annuloplasty prosthesis 104 is a generally rigid or inextensible prosthesis, for example as described in U.S. Pat. No. 6,183,512, issued to Howanec, et al, U.S. Pat. No. 5,350,420, issued to Cosgrove, et al., or U.S. Pat. No. 5,104,407, issued to Lam, et al., all incorporated herein by reference in their entireties. As described in these patents, the prosthesis 104 may be made inextensible by means of included plastic or metal tensile reinforcements or molded plastic or metal inserts.

While the prosthesis 104 as illustrated takes the form of an annuloplasty ring, the holder may also be used with a band. In such case, the pins 114 are preferably located so that they will pass through the band adjacent its ends.

Figure 7:
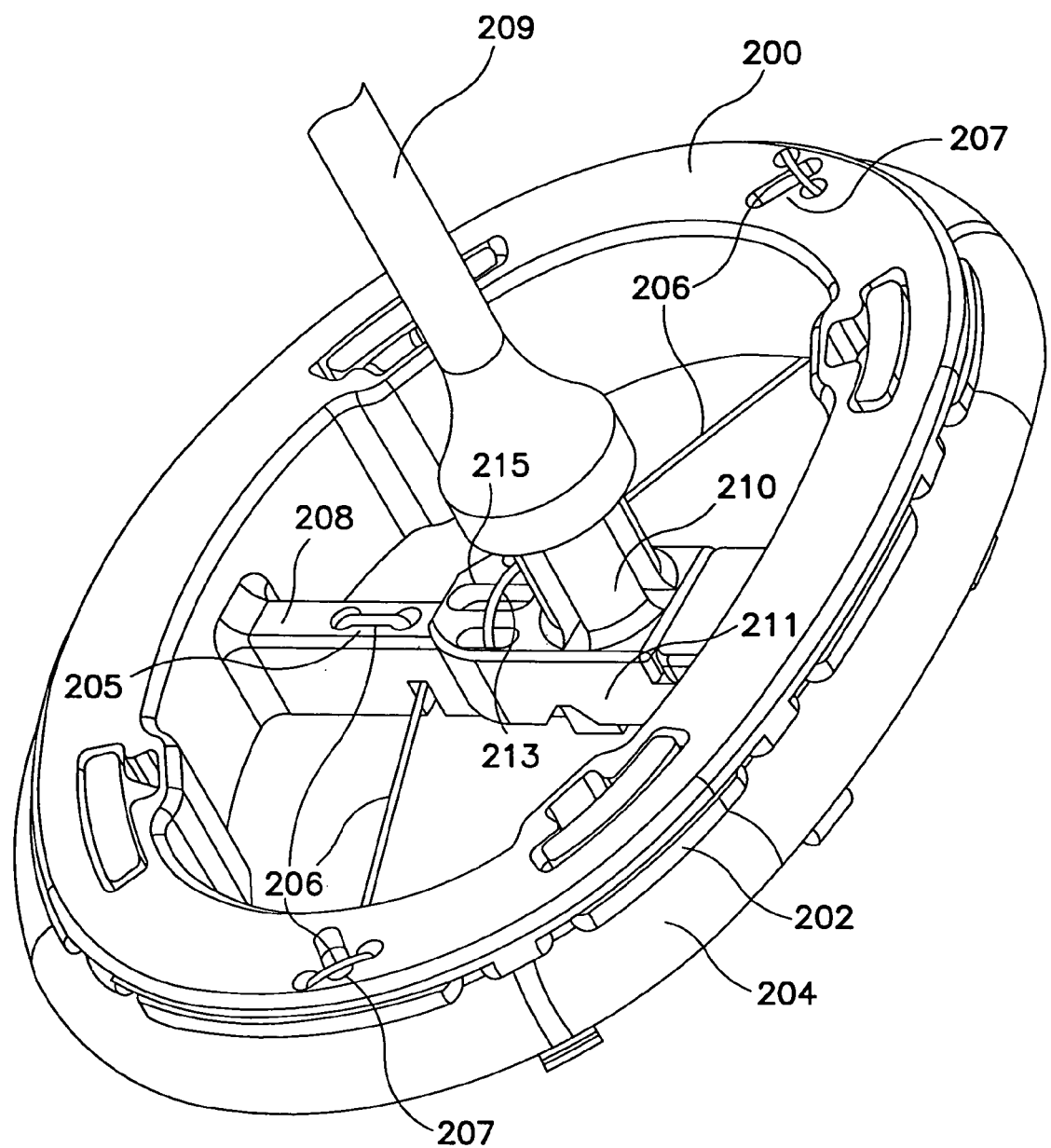
FIG. 7 is a perspective view of a two-component annuloplasty prosthesis holder according and associated handle according to a second embodiment of the present invention.

FIG. 7 is a perspective view of a second embodiment of a two-piece holder according to the present invention, with handle 209 attached. In this embodiment, annuloplasty prosthesis 204 is mounted against an outer circumferential surface of first holder component 202, which is in turn retained against second holder component 200. The second holder component 20 is provided with a snap fitting 210, engaging a pin on the end of the handle 209. The snap fitting may be replaced by a threaded recess or other mechanical mechanism for connecting to the handle 209. Snap fitting 210 is mounted to a removable base 211, which is retained to cross bar 208 of component 200 by means of suture 213, which is captured to base 211. Handle 209 and base 211 are removed together after cutting suture 213 at slot 215. Sutures 206 retain component 200 adjacent component 202. Sutures 206 are tied to component 200 in the vicinity of grooves 207 and 205. When cut at grooves 207, component 200 is released to move upward relative to component 202, in turn releasing the annuloplasty prosthesis 204, as described in more detail below.

In this view it can seen that substantial apertures are defined through the assembly comprising components 200 and 202, allowing for testing of the coaption of valve leaflets. The portions of sutures 206 extending across the apertures, between the edges of component 200 and cross bar 208 may be employed to assist the physician in repair of leaflets with damaged chordae tendonae, as discussed in more detail in conjunction with FIGS. 12A and 12B.

Figure 8:
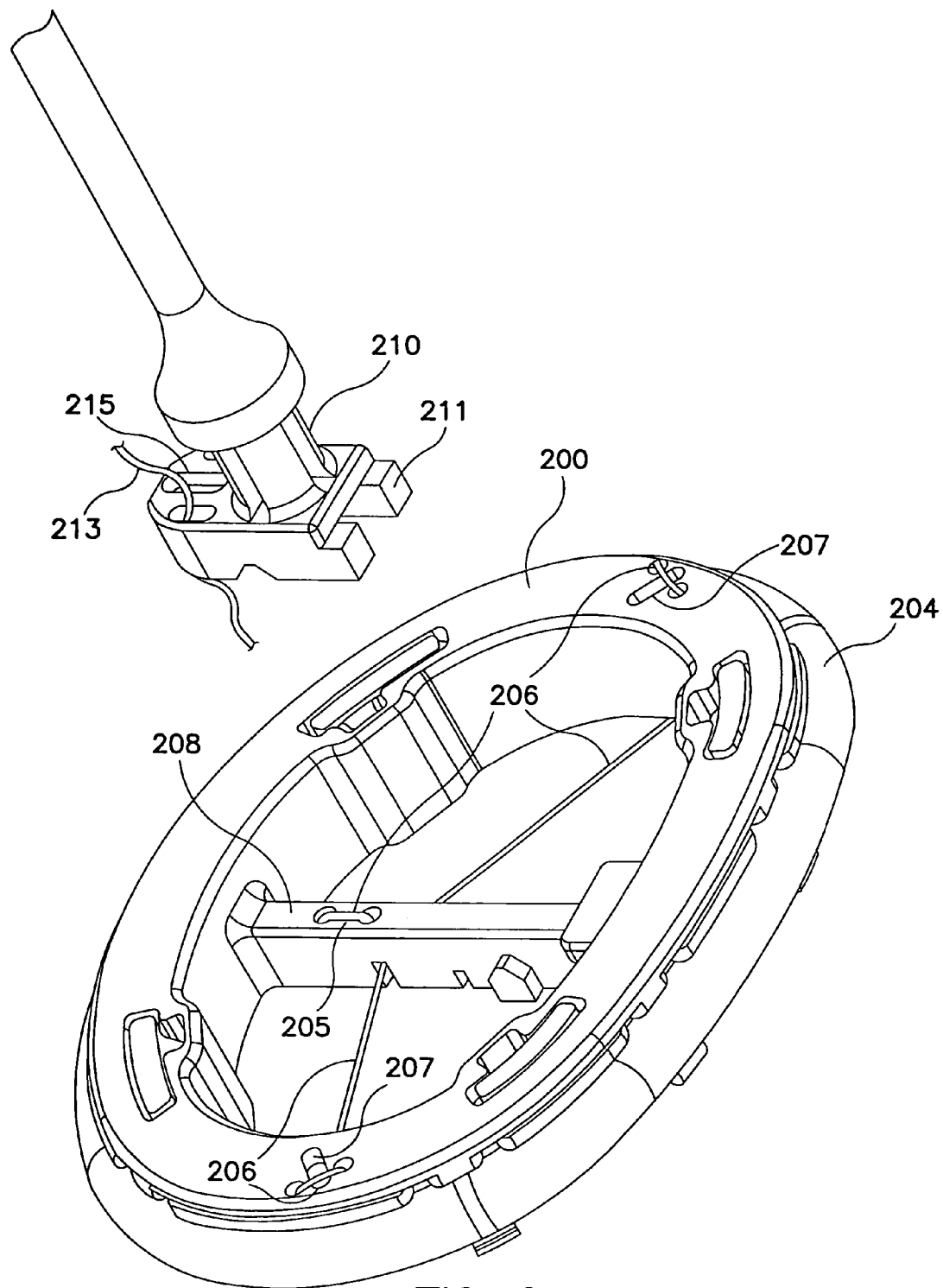
FIG. 8 is a perspective view from above of the embodiment of FIG. 7, with the handle removed.

FIG. 8 is a perspective view from above of holder components 202 and 200 and prosthesis 204 as illustrated in FIG. 7 showing removal of the handle 209 and base 211 after cutting of suture 213. While the preferred embodiment as illustrated employs a relatively small base 211 to which the handle is mounted, in alternative embodiments a template as discussed in conjunction with FIGS. 1 and 2, held to component 200 by cuttable sutures, might be substituted for base 211. Alternatively, base 211 might be omitted and snap-fitting 210 might instead be formed as part of the crossbar 208.

Figure 9:
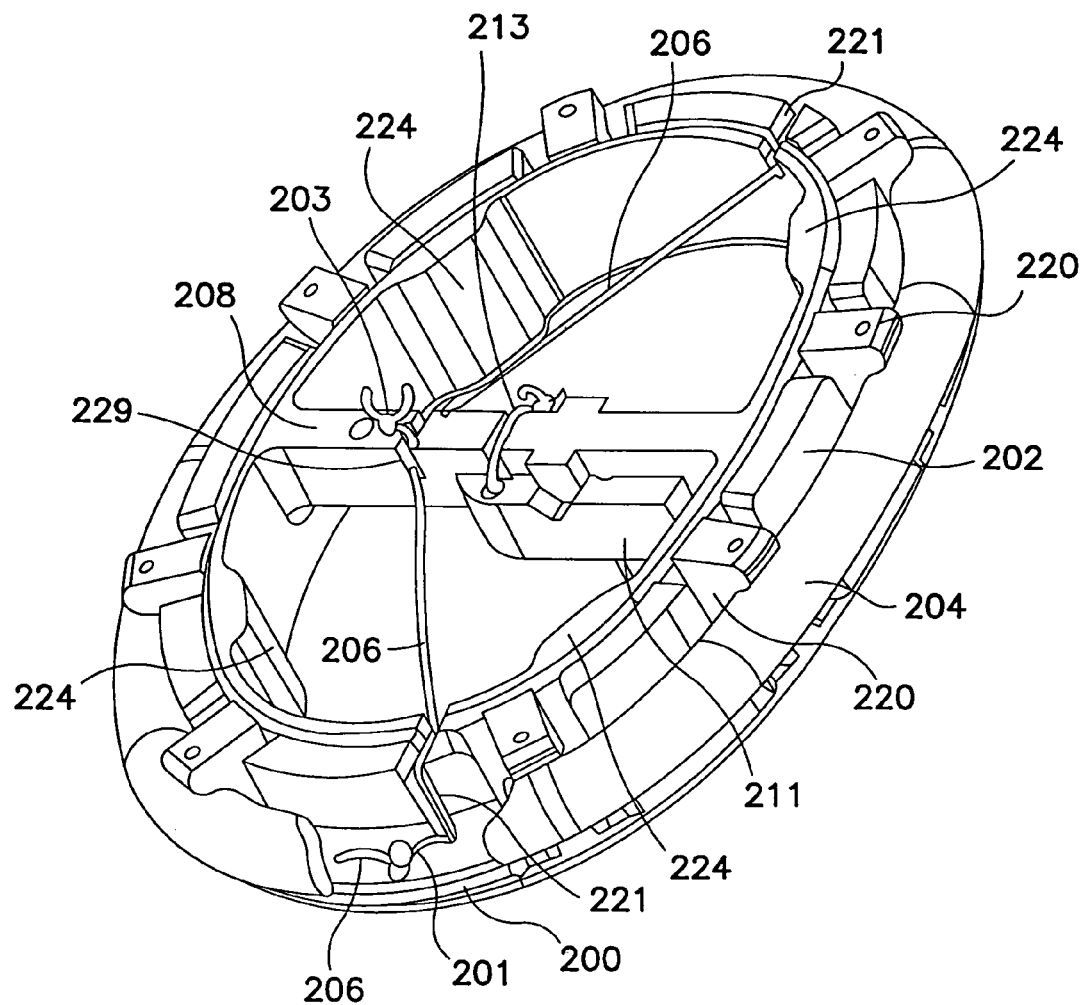
FIG. 9 is a perspective view from below of the embodiment of FIG. 7.

FIG. 9 is a view from below of the first and second holder components 202 and 200 in conjunction with the annuloplasty prosthesis 204. Numbered elements correspond to those in FIG. 7. In this view, the routing of the sutures 206 to retain first and second holder components 202, 200 closely adjacent to one another is further illustrated. Sutures 206 are tied to component 202 adjacent its outer periphery by knots 201, of which only one is visible. Free ends of sutures 206 then extend upward through component 200, across slots 207 (FIG. 7), back downward through component 200, along L-shaped slots 221 and across the apertures through component 202 to slot 229 in crossbar 208. Sutures 206 then pass upward through crossbar 208, along slot 205 (FIG. 7) back downward through crossbar 208 and are tied at knots 203 to retain them to the crossbar.

In operation, the first and second components of the prosthesis work in a fashion similar to the first and second components of the holder illustrated in FIGS. 3–6, discussed above. When first and second holder components 202, 200 are located closely adjacent to one another as illustrated, pins 214 (not visible in this view) extending downward from component 200 extend through prosthesis 204. Projections 220 extend radially outward from the first holder component 202 adjacent the lower surface of prosthesis 204 preventing downward movement of the prosthesis off of pins 214. This mechanical interrelation is illustrated in more detail in FIGS. 10 and 11A, discussed below. When released, component 200 can move upwardly enough to withdraw the pins 214 from prosthesis 204. Projections 220 are configured to allow them to bend inwardly after upward movement of component 200, facilitating removal of the prosthesis 204. This mechanism is also discussed in more detail in conjunction with FIGS. 10 and 11A. Holder components 200 and 202 are mechanically captured to one another by means of interacting tabs and grooves in regions 224 of the holder, described in more detail in conjunction with FIG. 12B.

Figure 10:
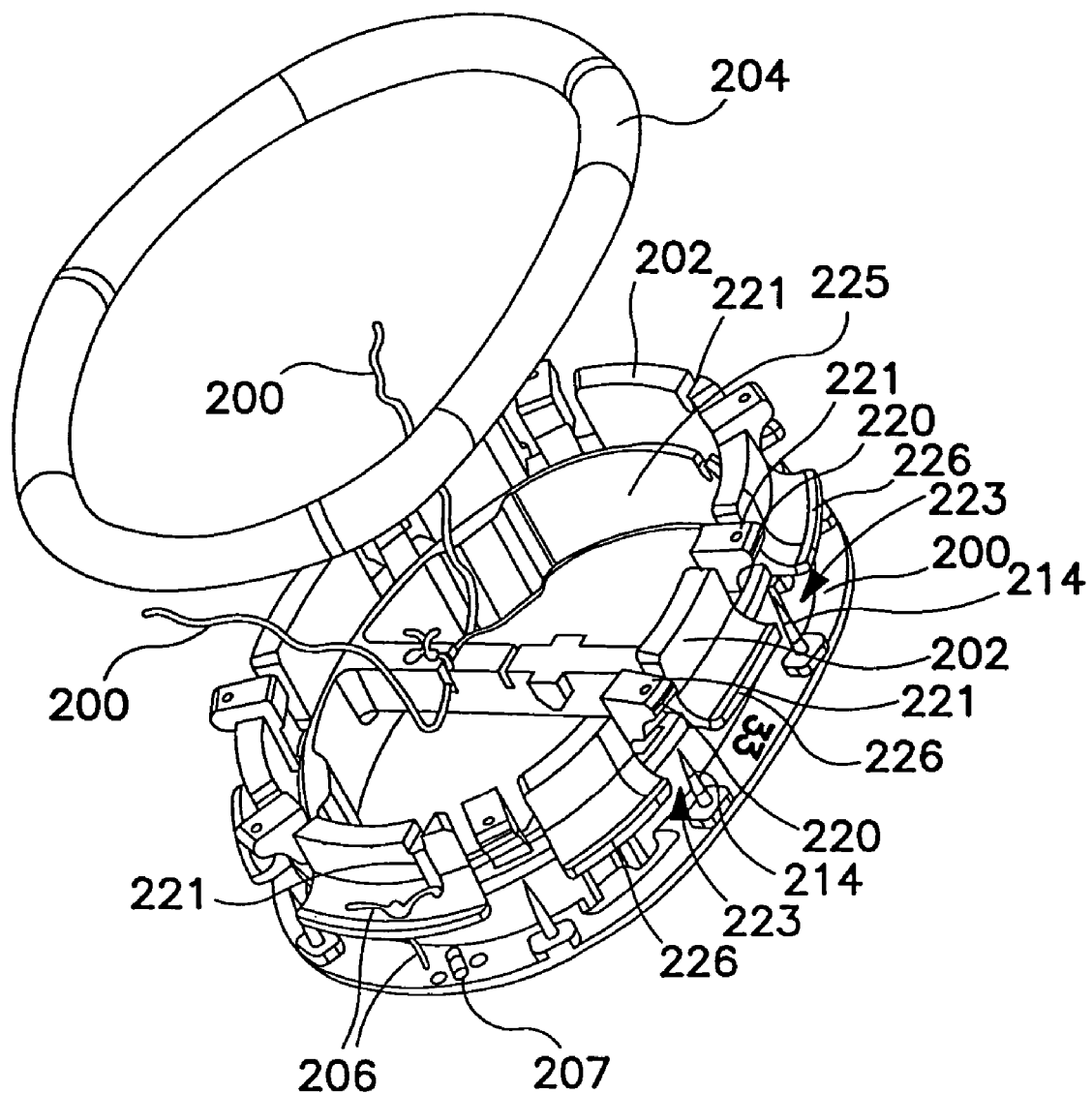
FIG. 10 is a perspective view from below of the embodiment of FIG. 7 illustrating the second component moved upwardly from the first component to release the annuloplasty prosthesis.

FIG. 10 is a view from below of the first and second holder components 202 and 200 in conjunction with the annuloplasty prosthesis 204. Numbered elements correspond to those in FIGS. 7–9. In this view, sutures 206 have been cut at slots 207, allowing for holder component 200 to be moved slightly upwardly from holder component 202. Holder component 200 has moved upwardly enough to withdraw pins 214 from prosthesis 204. The prosthesis 204 is removed over projections 220, leaving it positioned adjacent to valve annulus. In this view, it can be seen that pins 214 extend through openings or interruptions 223 in the circumferential flange 226 located adjacent the upper edge of component 202. As illustrated in more detail in FIG. 11A, projections 220 can pivot inwardly, facilitating removal of the prosthesis 204 from the holder after circumferential wall 228 of component 200 has moved upward of the projections 220 and no longer prevents their inward motion.

In the specific embodiment illustrated, pins 214 extend all the way through the prosthesis 204 and into corresponding holes 221 in the lower, radially extending projections 220. In other embodiments, pins 214 may be shortened and need not extend all the way to or into the lower radially extending projections 220. As discussed above, extension of the pins 214 to or preferably into the projections 120 may be especially desirable if the annuloplasty prosthesis 204 is very flexible and or extensible and may be less beneficial if the annuloplasty prosthesis 204 is a generally rigid or inextensible prosthesis. While the prosthesis 204 as illustrated takes the form of an annuloplasty ring, the holder may also be used with a band. In such case, the pins 214 are preferably located so that they will pass through the band adjacent its ends.

Figure 11A:
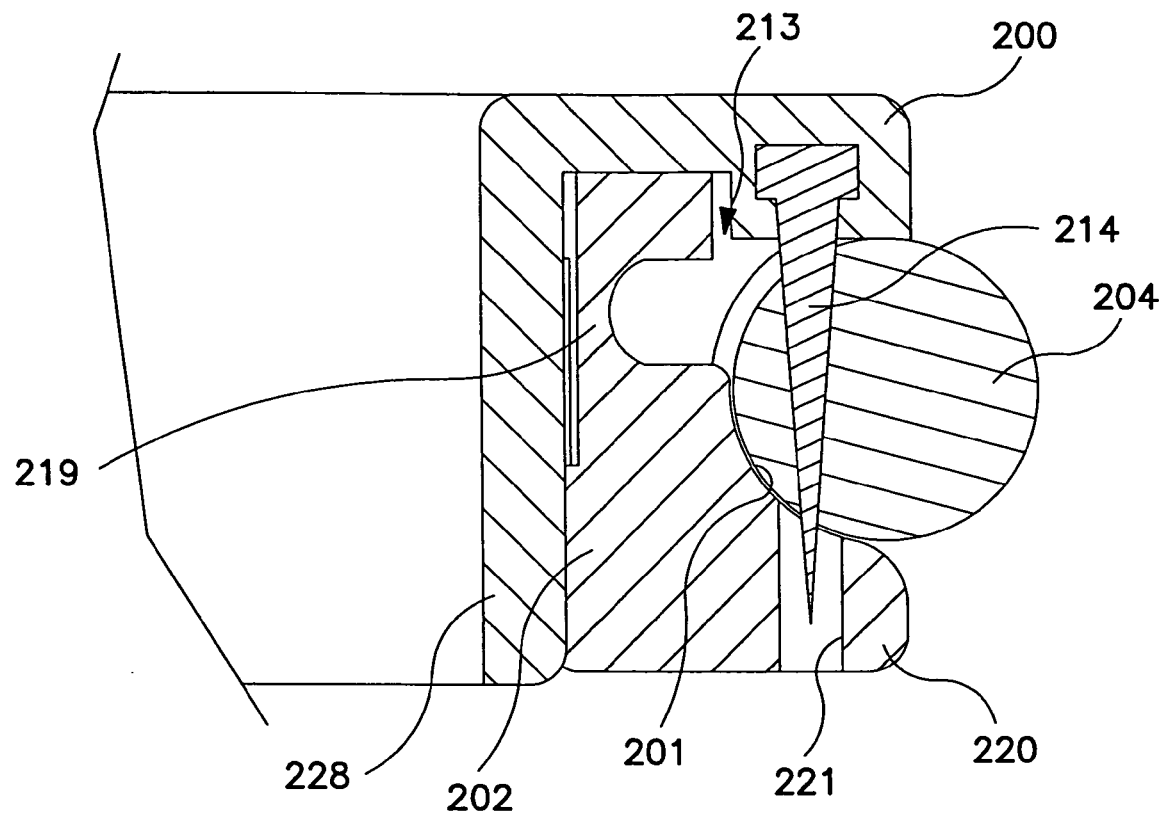
FIGS. 11A and 11B are a cross sectional views through portions of the first and second components of the embodiment of FIG. 7, illustrating interconnection of the prosthesis and the holder components.

FIG. 11A illustrates a cross-sectional view through a portion of the combination of first holder component 200, second holder component 202 and the prosthesis 204. In this view, illustrating the situation prior to upward movement of the second holder component. Pin 214 passes through the aperture 223 in the outwardly extending flange 226 (FIG. 10) of upper component 220, extends through prosthesis 204 and terminates in hole 221 in projection 220. Outwardly extending projection 220 prevents downward movement of the prosthesis 204 off of pin 214. Preferably, the thickness of first component 200 is reduced at 219 to define a hinge point, allowing projection 220 to pivot inward after upward movement of circumferential wall 228 has occurred.

Figure 11B:
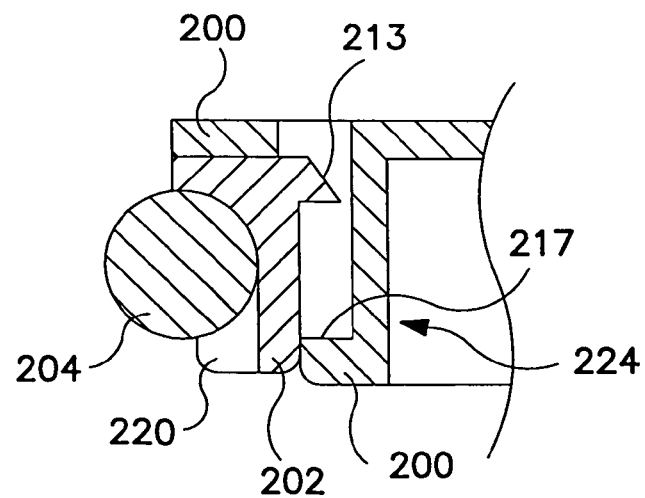

FIG. 11B illustrates a cross-sectional view of a portion of the assembly comprising first and second holder components 202, 200 and prosthesis 204. This cross-section is taken through one of the regions 224 illustrated in FIGS. 9 and 10. Holder components 200 and 202 are retained to one another by projections or tabs 213 located slidably within grooves 215, allowing upward movement of second component 200 until the lower end of 217 of groove 215 contacts the projection 213. This mechanism limits upward movement of the second holder component 200 and retains first and second holder components 200, 202 together, as illustrated in FIG. 10.

FIGS. 12A and 12B are cut-away views illustrating the utility of sutures 206 in conjunction with surgical repair of broken chordae tendonae (chords), as is sometimes performed in conjunction with placement of an annuloplasty prosthesis. The basic procedure involved is described in the article "Surgical Techniques For The Repair Of Anterior-Mitral Leaflet Prolapse" by Duran, published in the Journal Of Cardiovascular Surgery, 1999; 14:471–481, incorporated herein by reference in its entirety. As illustrated in FIG. 12A, a double-armed suture 252 is first attached to the papillary muscle 256 by means of a pledget 258. Alternatively, as described in the Duran article, if multiple chords are to be replaced, a loop of suture may be attached to the papillary muscle and multiple double-armed sutures passed through the loop for attachment to the valve leaflet or leaflets. Suture 252 is intended to replace the broken chord 255. The free ends of the suture 252 are passed upward and sutured to the edge of valve leaflet 250, previously attached to the papillary muscle 256 by means of the broken chord.

In the procedure as described in the above cited Duran article, adjustment of the height of the leaflet 250 to determine proper placement of knots 254, coupling the sutures 252 to the leaflet 250 was accomplished by means of an additional suture passed through the leaflet, held upward by means of forceps to adjust the appropriate leaflet height. In conjunction with the present invention, after the annuloplasty prosthesis 204 has been moved downward and sutured to the valve annulus, suture 206 is used as a guide for determining the proper point at which knots 254 are tied, to assure that the leaflet 250 will coapt properly with the adjacent leaflet 251. Knots 254 comprise a series of knots, the first of which is tied around suture 206. The remaining knots are tied thereafter. One or more repairs of this type may be made along the portions of suture 206 extending across the apertures through the annuloplasty prosthesis holder, depending upon the number of chords that are broken. In the embodiment as illustrated in FIGS. 7–9 above, the path of the sutures 206 as they cross the apertures through the annuloplasty holder is intended to generally approximate the line of coaption of the leaflets of a mitral valve, facilitating their use in this particular surgery. Other possible routings for the sutures 206 might be substituted in conjunction with other possible valve repair surgeries.

FIG. 12B illustrates the production of knots 254 to anchor sutures 252 to the valve leaflet 250 in more detail. In this view it can be seen that one of the free ends of the suture 252 is passed upward through the valve leaflet, around the edge of the valve leaflet and through the leaflet again, while the other free end is simply passed up through the valve leaflet. The free ends are knotted together around suture 206 and the series of knots is continued until an adequate number of knots are provided to safely anchor the suture 252 to the valve leaflet 250.

After the leaflet repair is complete, sutures 206 are cut at slots 207 (FIG. 7) as discussed above to allow annuloplasty holder component 200 to move upward relative to component 202 (FIG. 10) to release the prosthesis 204. This also allows the cut ends of the sutures 206 to be pulled through the knot or knots 254, as the holder assembly is moved upward away from the valve annulus. While sutures 206, provide a preferred mechanism for facilitating the repair procedure discussed above, it is possible that other structures could be substituted for them, including other types of tensile members or more rigid members such as rods or bars, provided that provision is made for removal of the structures from the knots 254, after the surgical repair is complete.

Figure 13:
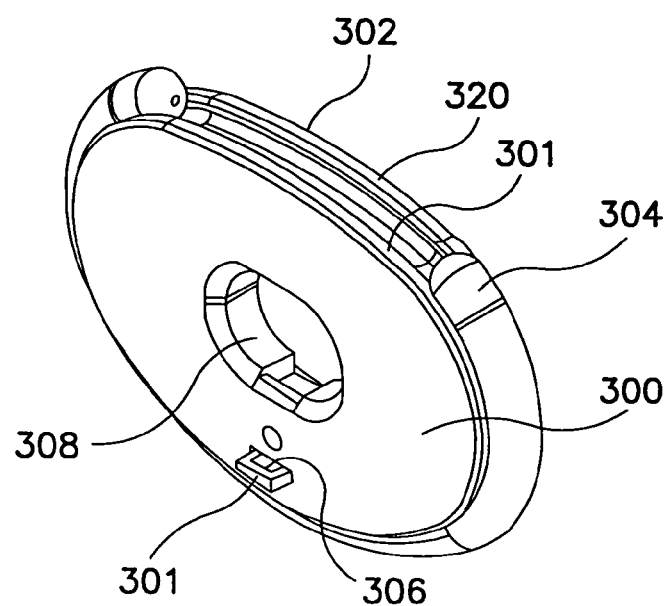
FIG. 13 is a perspective view from above of a two-component annuloplasty prosthesis holder according to a third embodiment of the present invention.

FIG. 13 is a perspective view of a third embodiment of a two-component annuloplasty prosthesis holder according to the present invention. The holder of FIG. 13 operates in a fashion similar to the operation of the holders discussed above, maintaining the annuloplasty prosthesis 304 adjacent the outer circumferential surface of the first holder component 302 by means of barbs extending downwardly from second holder component 300 and into prosthesis 304. The first and second holder components 302 and 300 are retained adjacent to one another by means of a suture (not illustrated in this view) passing through aperture 306 in tab 301, extending upward from the first holder component 302. The prosthesis 304 is prevented from moving downwardly off of the barbs extending downward from second holder component 300 by means of circumferential ridge 320, extending radially outward from the first holder component 302, adjacent the lower surface of prosthesis 304. The interrelation of the various components is illustrated in more detail in FIGS. 17 and 18, discussed below.

Figure 14:
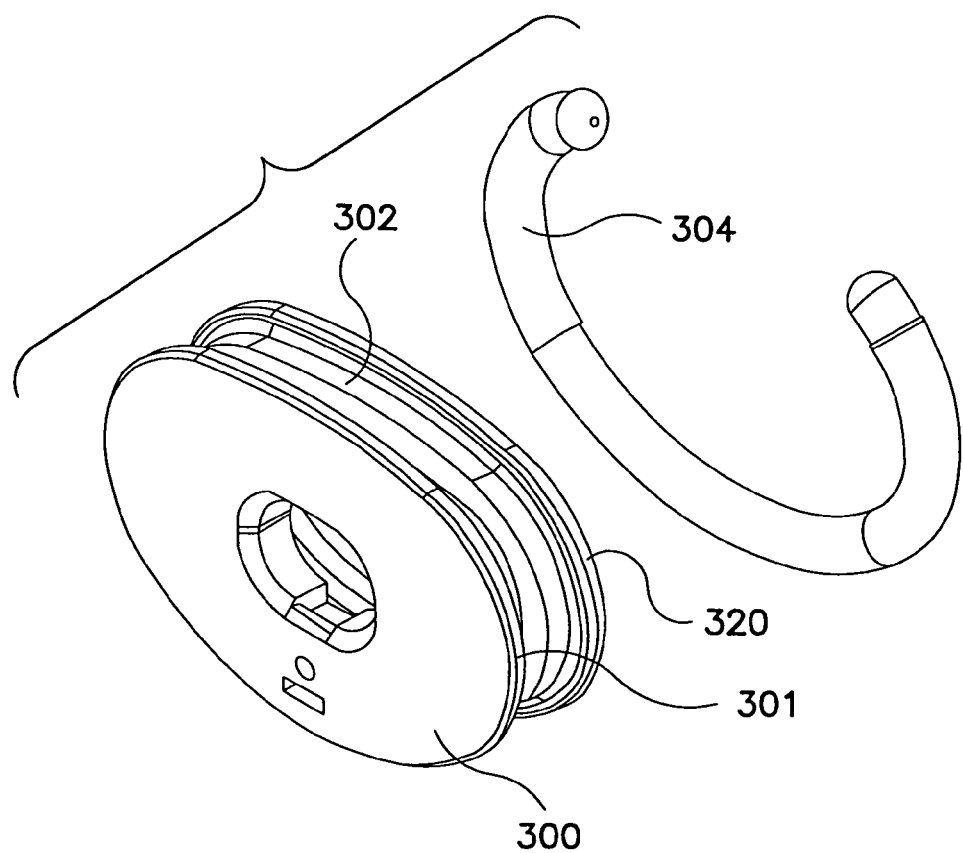
FIG. 14 is a perspective view of the embodiment of FIG. 13, illustrating movement of the second component upwardly relative to the first component to release the annuloplasty prosthesis from the holder.
Figure 15:
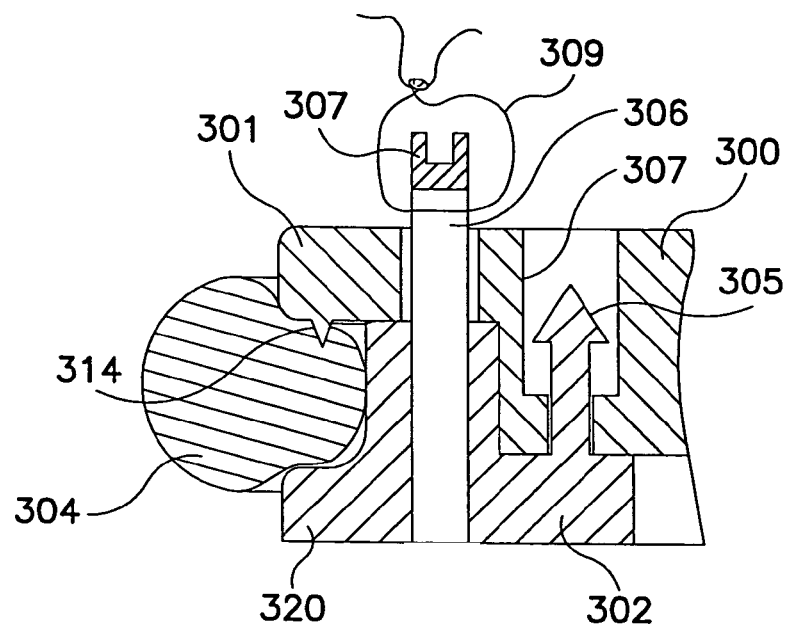
FIG. 15 is a cross sectional view through a portion of the first and second components of the embodiment of FIG. 13, illustrating the mechanism by which the prosthesis is retained upon the holder.
Figure 16:
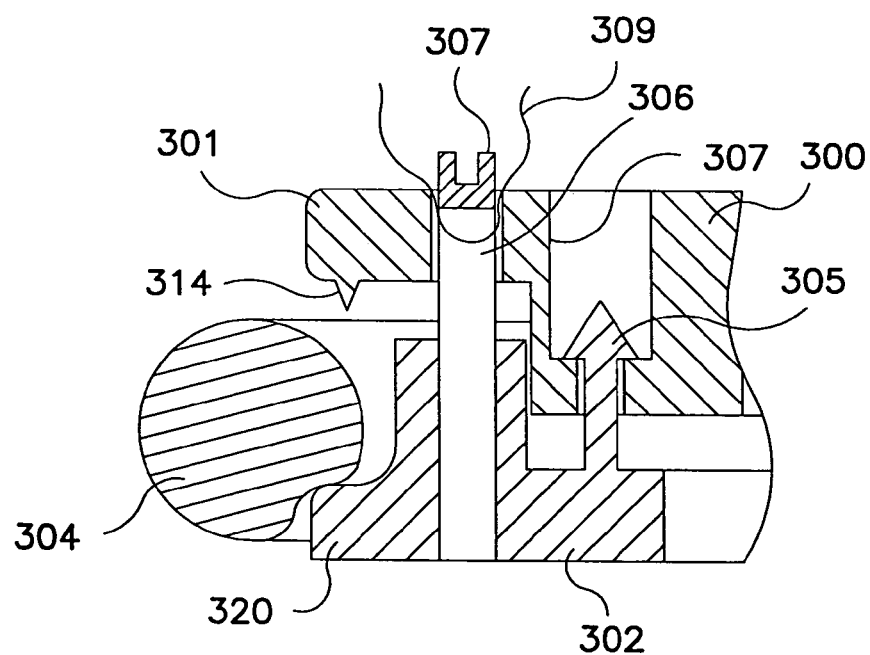
FIG. 16 is a cross sectional view through the same portion of the first and second components as illustrated in FIG. 15, showing upward movement of the second component relative to the first component and release of the annuloplasty prosthesis.

FIG. 14 shows the first and second holder components 302 and 300, after cutting of a suture extending through lug 301 (FIG. 13), allowing movement of the second holder component 300 upwardly from the first holder component 302. In this configuration, the barbs entering the annuloplasty prosthesis 304 are now removed from the prosthesis, allowing removal of the prosthesis 304 from the outer circumferential surface of first holder component 302. This operation, is illustrated in more detail in FIGS. 15 and 16, discussed below FIGS. 15 and 16 are cross-sectional views through the portion of the assembly comprising first and second holder components 300 and 302 and prosthesis 304. This view, taken through the assembly in the vicinity of tab 301, shows suture 309 passing through the aperture 306 in the tab, preventing upward movement of the second component 300 relative to the first component. Downwardly extending barb 314 extends down from the second holder component 300 into the annuloplasty prosthesis 304 which is prevented from downward movement relative to barb 314 by radially extending flange 320, located adjacent to lower edge of prosthesis 304. Barbs 314 are located at intervals extending around component 301. In cases in which the prosthesis is a band, as illustrated, it is desirable that projections 314 be located to engage the band near its ends. As the projections do not extend through the prosthesis to the ridge 320, this embodiment as illustrated might be most useful with annuloplasty bands that are inextensible, as described above. However, the embodiment as illustrated might still be useful with annuloplasty rings or bands that are somewhat extensible. Alternatively, extension of the barbs 314 to reach or enter the ridge 320 might make the holder more useful with extensible bands and rings.

First and second holder components 302, 300 are retained to one another by means of a mechanism comprising an upwardly extending barb 305, located in bore 307 formed within the second holder component 300. Upward movement of the second holder component 300 is terminated upon engagement of the barb 305 with the lower surface of the boor 307. FIG. 16 shows the upward limit of movement of the second holder component 300 relative to the first holder component 302. All labeled elements in FIG. 16 correspond to those in FIG. 15.

Figure 17:
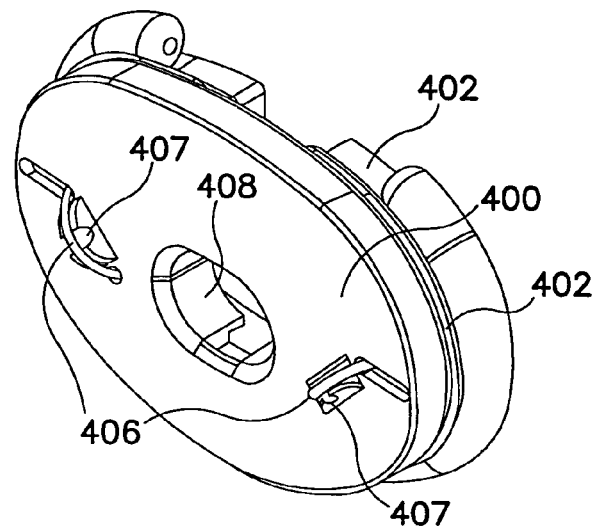
FIG. 17 is a perspective view from above of a two-component annuloplasty prosthesis according to a fourth embodiment of the present invention.

FIG. 17 is a perspective view from the top surface of a fourth embodiment of a two-piece annuloplasty prosthesis holder according to the present invention. In this case, the prosthesis 404 is mounted around the circumferential surface of the first component 400, which is releasably secured to the second component 402 by means of sutures 406, cuttable at slots 407. In this embodiment, the second component 402 merely serves as a template, in a fashion analogous to that discussed in conjunction with the prior art Medtronic prosthesis described in conjunction with FIGS. 1 and 2 above, and does not participate in retention of the prosthesis 404 to the first component 400. Second component 402 is provided with an aperture 408 for releasably engaging a handle which may correspond to handle 16, FIG. 1.

Figure 18:
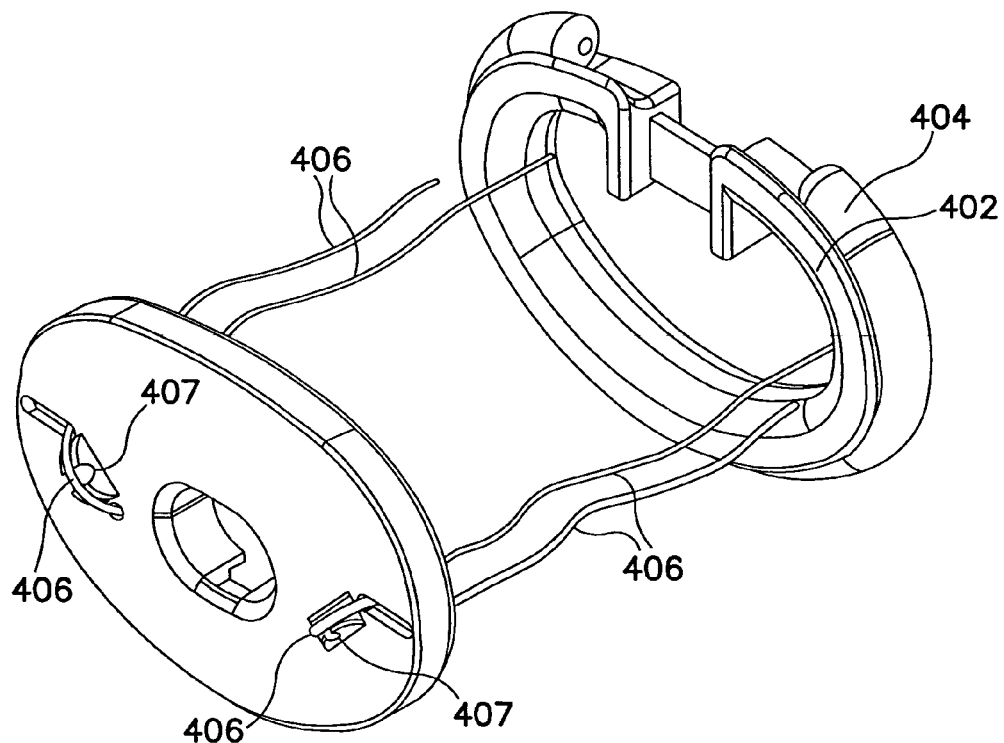
FIG. 18 is a perspective view illustrating separation of the first and second components of the embodiment of holder of FIG. 17.
Figure 19:
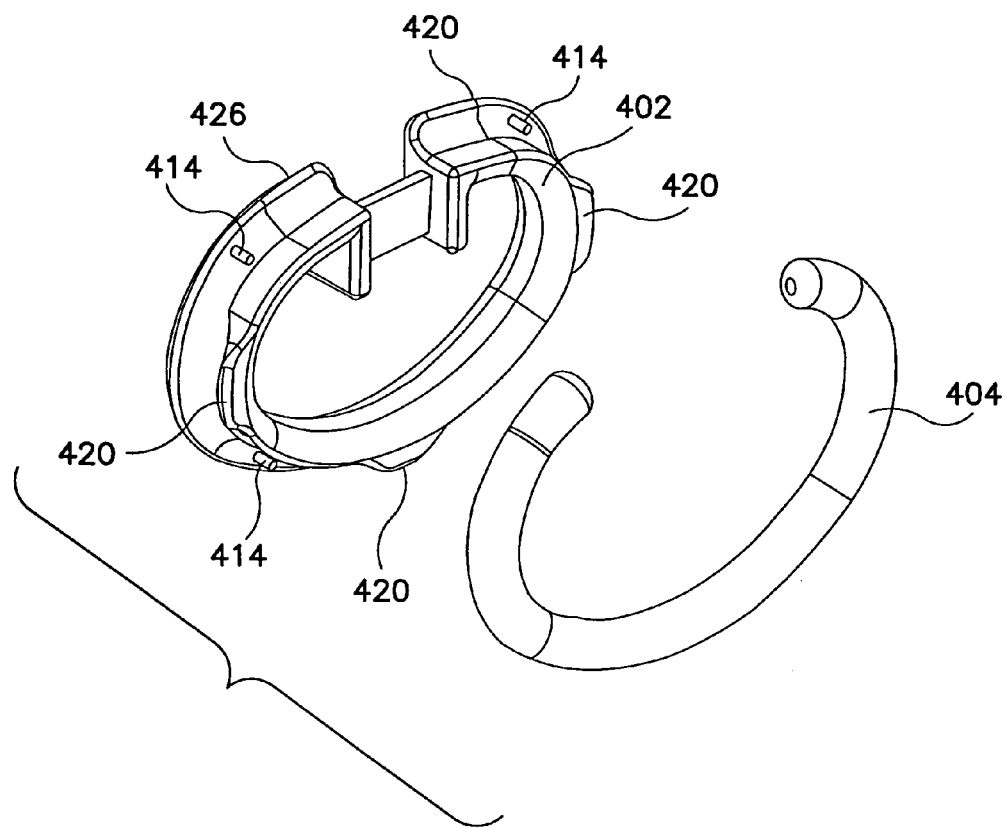
FIG. 19 illustrates the first component of the embodiment of FIG. 18, with the annuloplasty prosthesis removed.

FIG. 18 is a perspective drawing from the upper surface of the holder assembly of FIG. 19, illustrating a schematically the inter-relation of the first and second holder components 402, 400, and the interconnection by means of sutures 406. Of course, when assembled sutures 406 are drawn to tightly hold the first and second components together and their ends are captured in the second holder component 400. In this view it can be seen that the first holder component 402 is provided with a circumferential, outwardly extending upper edge 403 which carries downwardly extending pins (not visible in this view), which penetrate into the prosthesis 404 and assist in retaining it on the first holder component 402. The mechanism of retention of the prosthesis 404 is illustrated in more detail in FIG. 21.

FIG. 19 is a perspective view of the first holder component 402, viewed from the lower side of the component, with the prosthesis 404 removed. In this view it can be seen that pins 414 are provided, extending downwardly from radial flange 403. Also provided are radially extending projections 420, which extend outward from the first component 402, along side the lower surface of prosthesis 404 when it is mounted around the circumferential surface of holder 402. Although in this embodiment, the projections 420 are not located directly opposite corresponding ones of the pins 414, they none the less operate in a similar fashion to maintain the prosthesis 404 mounted to the first component 402 of the holder. This particular embodiment of the holder of the present invention is particularly suited for use with annuloplasty bands, with the pins 414 embedded in the prosthesis 404 close to ends 405 of the band. Removal of the band from the first holder component is accomplished by first moving the ends 405 of the band 404 off of the pins 414 adjacent the ends of the band. This then allows the band to expand outwardly over and around adjacent projections 420, with corresponding removal of the band from the remainder of the pins 414 and projections 420 accomplished in a similar fashion.

As the pins 414 do not extend through the prosthesis to projections 420, this embodiment as illustrated might be most useful with annuloplasty bands that are inextensible, as described above. However, the embodiment as illustrated might still be useful with annuloplasty rings or bands that are somewhat extensible.

Figure 20:
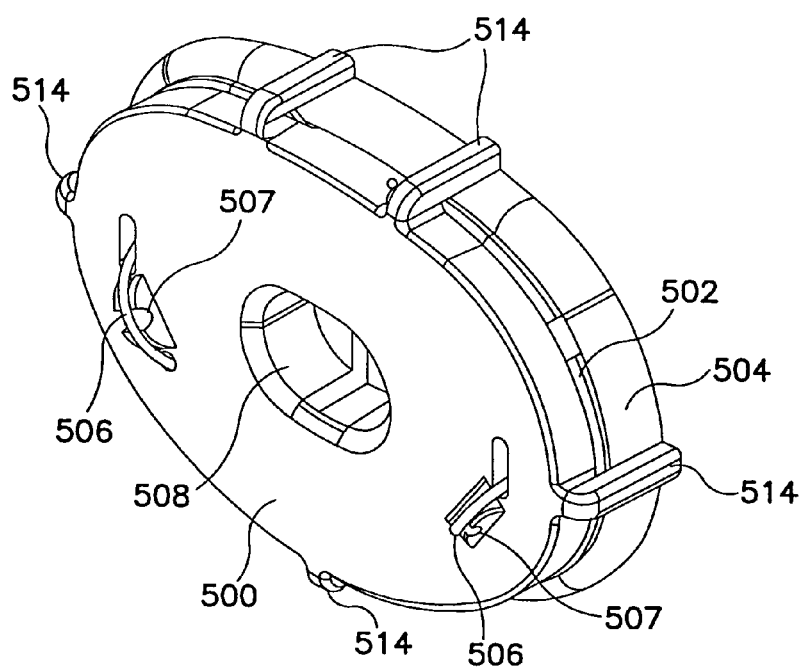
FIG. 20 is a perspective view from above of a two-component annuloplasty prosthesis holder according a fifth embodiment of to the present invention.

FIG. 20 is a perspective view of a fifth embodiment of a two-component holder according to the present invention. In this version of the invention, the prosthesis 504 is mounted around a outer circumferential surface of the first component 502, but is retained by a mechanism not requiring pins or other structures penetrating into the prosthesis itself. As in the embodiments above, the second holder component 500 is secured to the first holder component 502 by means of sutures 506, cuttable at slots 507, allowing for release of the second holder component 500 and upward movement of the second holder component relative to the first holder component in a manner similar to that discussed above in conjunction with the embodiment illustrated in FIGS. 3–6. The second component 500 is provided with downwardly extending fingers 514 which operate in conjunction with projections (not visible in this view) on the first component 502 to retain the prosthesis 504 to the holder. The construction of the holder and the mechanism by which prosthesis is maintained is illustrated in more detail in FIGS. 21–22.

Figure 21:
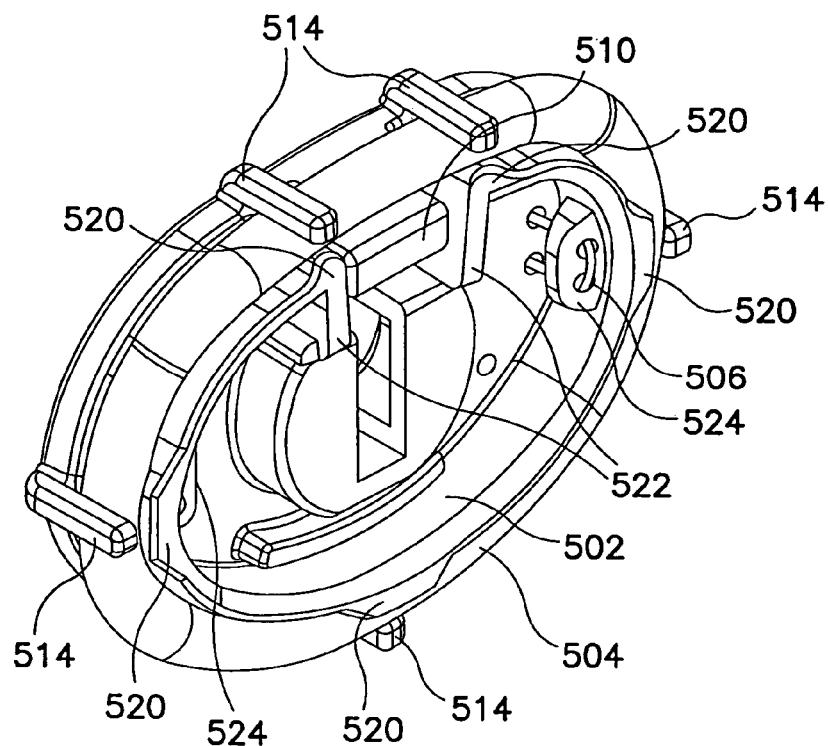
FIG. 21 is a second perspective view from below of the embodiment of FIG. 20.

FIG. 21 is a perspective view showing the lower surface of the holder of FIG. 20. In this view it can be seen that sutures 506 pass through holes in tabs 524 to retain the first and second components 502, 500 together, in the fashion discussed above. In this view it is also apparent that the first holder component 502 corresponds generally to the construction of the first holder component 102 of the embodiment illustrated in FIGS. 3–6, discussed above. The first component 502 is similarly configured as an open ring, provided with inwardly extending projections 522 adjacent its open ends, which in turn are prevented from being moved toward one another by means of rectangular projection 510, extending downward from the second component 500, preventing movement of the projections 520 toward one another.

The prosthesis 504 is maintained to the holder assembly by the interaction of the downwardly extending fingers 514 and the radially extending projections 520, spaced around the periphery of the first holder component 502. With the first and second components adjacent one another, downwardly extending fingers prevent movement of the prosthesis 504 outward away from the circumferential outer edge the first component 502 and outwardly extending projections 520, adjacent the lower surface of prosthesis 504, prevent downward movement of the prosthesis away from fingers 514. As in conjunction with the embodiment illustrated in FIGS. 3–5, above, cutting of sutures 506 allows for upward movement of the second holder component 502, removing rectangular projection 510 from between the inwardly directed projections 522 of the first holder component 502.

Figure 22:
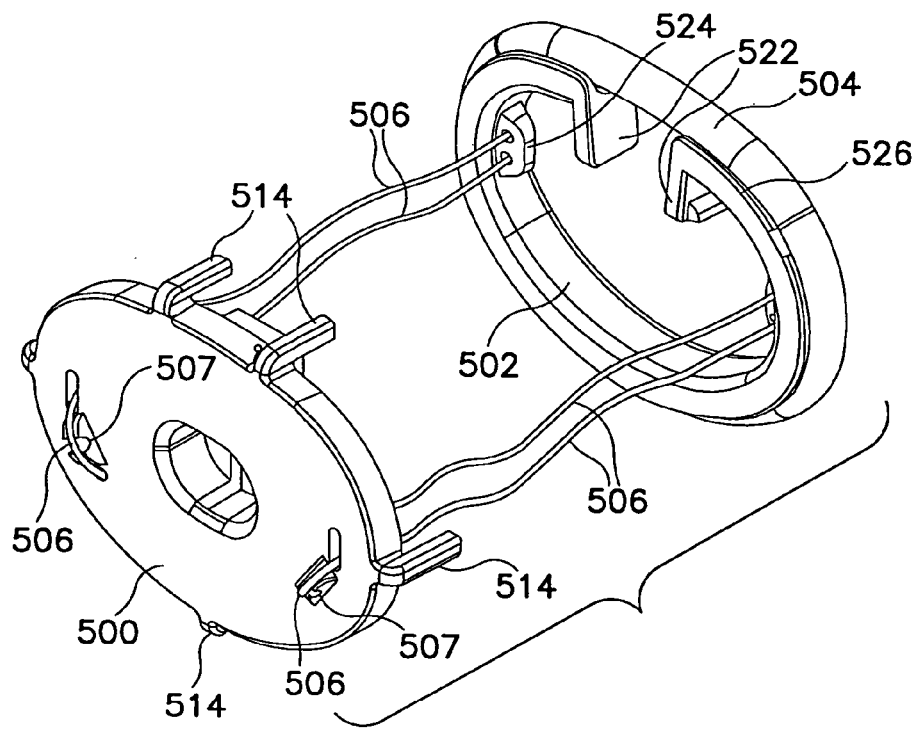
FIG. 22 is a perspective view of the embodiment of FIG. 20, with the first and second components separated from one another.
Figure 23:
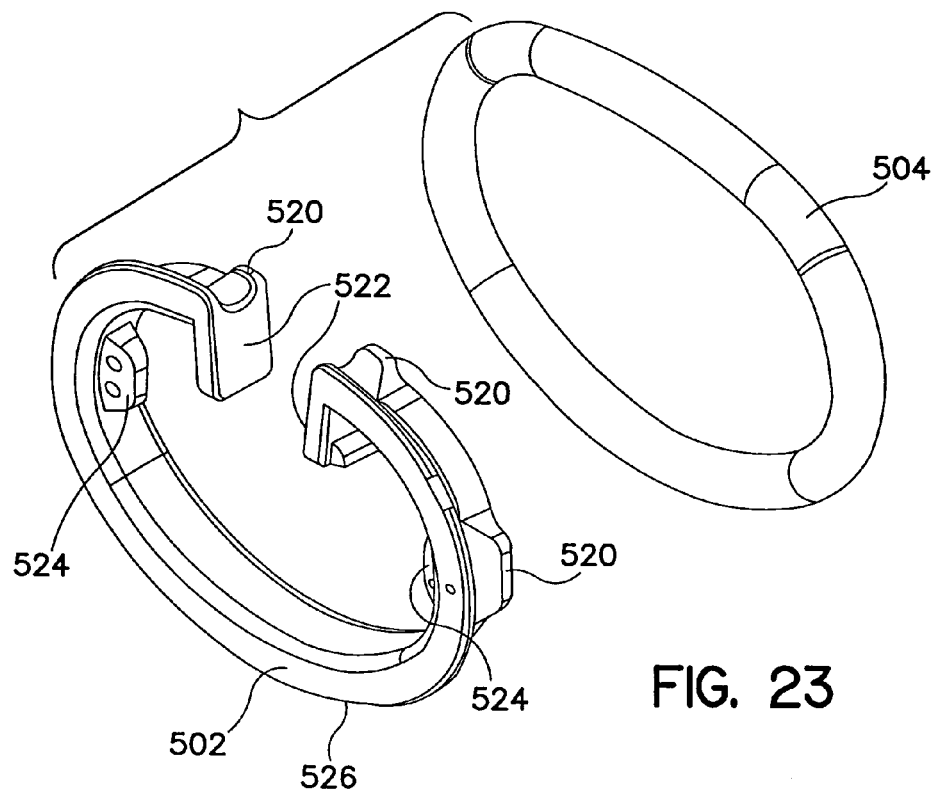
FIG. 23 is a perspective view of the first component of the embodiment of FIG. 20, with the annuloplasty prosthesis removed from the holder.

The system of the first and second components and prosthesis is illustrated with the second component moved upwardly away from the first component in FIG. 22, in which numbered elements correspond to those illustrated in FIGS. 20 and 21, discussed above. Once the second component 500 is removed from first component 502, the inwardly directed projections 522 may be squeezed by means of a forceps or hemostat, reducing the outer circumference of the first holder component 502 and facilitating removal of the prosthesis. The first component 502 with the prosthesis 504 removed is illustrated in FIG. 23. All numbered elements correspond to those illustrated in FIGS. 21–22.

This particular embodiment of the invention as illustrated may be most useful in conjunction with annuloplasty rings, but may also be useful in conjunction with annuloplasty bands. If used with annuloplasty bands, penetrating members of some sort might usefully be added, located to engage the prosthesis adjacent its ends, as discussed above.

Figure 24:
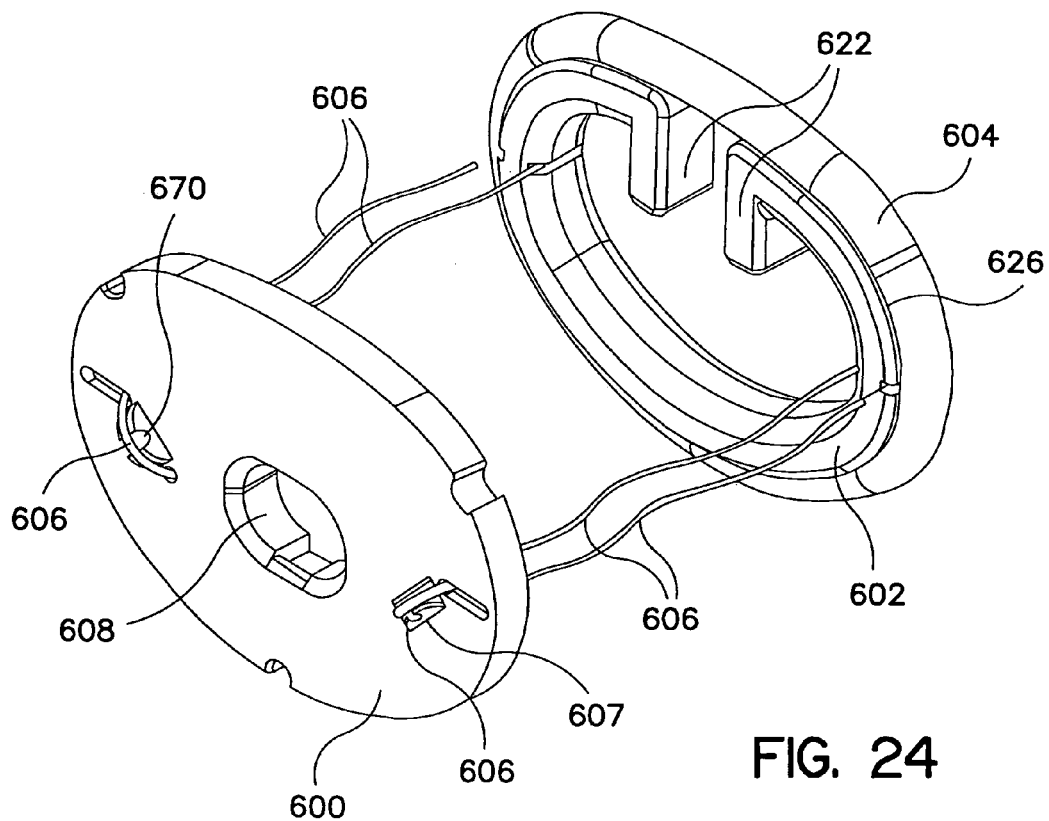
FIG. 24 is a perspective view from above of a two-component annuloplasty prosthesis holder according to a sixth embodiment of to the present invention.

FIG. 24 is a perspective view of a two-piece holder according to a sixth embodiment of the present invention. The embodiment of FIG. 24 operates in a fashion similar to that of the embodiment illustrated in FIGS. 20–23, discussed above, the primary difference being that the second holder component 600 is not provided with downwardly extending fingers, as illustrated at 514 in FIG. 22, discussed above. The first component 600 is initially retained adjacent the second 602 by means of sutures 606, cuttable at slots 607, which operate in a fashion similar to the cuttable sutures 506 discussed in conjunction with FIG. 22, above. Like the first component 502 discussed above, first component 602 takes the form of an open ring having inwardly projections 622 adjacent its ends. Projections 622 may be squeezed inwardly to reduce the outer circumference of the first holder component 602, facilitating removal of the prosthesis 604. Although not visible in this view, it should be understood that the second holder component 600 is provided with a downwardly extending rectangular projection corresponding to projection 510 as illustrated in FIG. 21, which in a similar fashion prevents inward movement of projections 622 when the first and second holder components are secured adjacent to one another by means of sutures 608. In this view it can be seen that the first holder component 602 is provided with a radially extending, circumferential flange 626, extending along the upper surface of the prosthesis 604. Not visible in this view is a second corresponding circumferential flange extending from the first holder component 602, adjacent the lower surface of the prosthesis 604. The prosthesis 604 lies in the groove defined between these upper and lower flanges, and is released from the groove by the physician's squeezing projections 622 and 624 toward one another, in a fashion corresponding to that discussed in conjunction with the embodiment of FIGS. 20–23, above.

Figure 25:
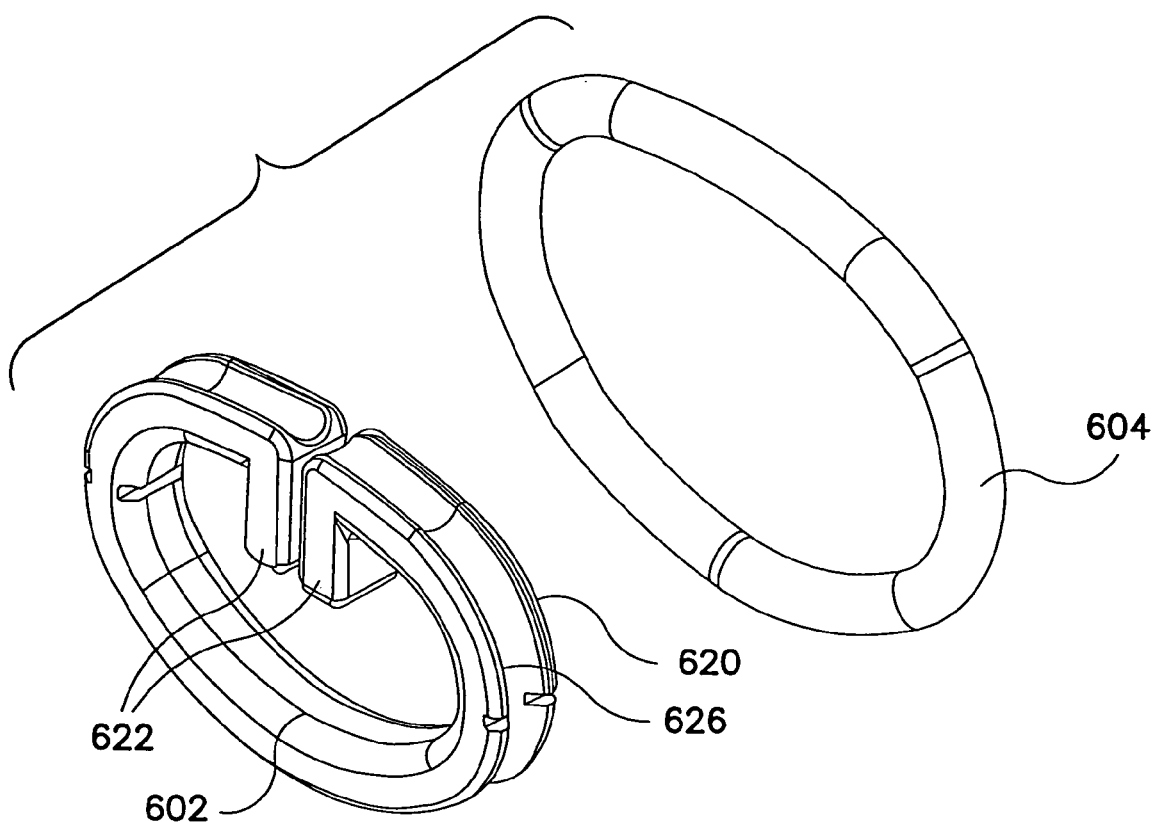
FIG. 25 is a perspective view illustrating removal of the annuloplasty prosthesis from the embodiment of FIG. 24.

FIG. 25 illustrates the first component 602 with the annuloplasty prosthesis 604 removed. In this view, inwardly directed projections 622 have been squeezed toward one another to release the prosthesis. In this view, the lower, radially extending flange 620 is also visible, as is the groove extending around the circumferential surface of the first component 602, in which the prosthesis 604 was mounted.

This embodiment as illustrated is probably most useful in conjunction with inextensible annuloplasty rings as discussed above. However, it may also be useful in conjunction with somewhat extensible annuloplasty rings or with relatively rigid annuloplasty bands, as also discussed above.

Figure 26:
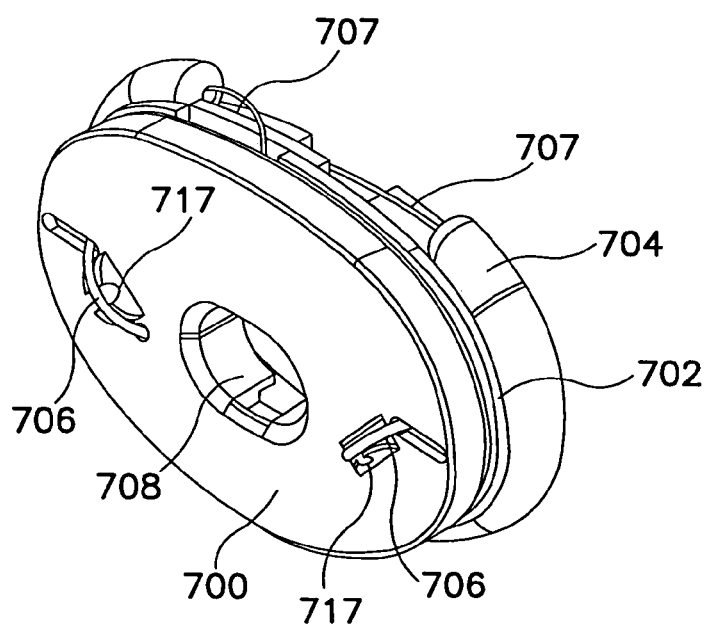
FIG. 26 is a perspective view from above of a two-component annuloplasty prosthesis holder according a seventh embodiment of to the present invention.

FIG. 26 is a perspective view showing the upper surface of a seventh embodiment of a prosthesis holder according to present invention. In this case, the second component 700 may correspond to the second component 600, illustrated in FIG. 24 and discussed above. The second component is retained to the first component 702 by means of sutures 706, cuttable at slots 717, in a similar fashion. However, in this embodiment, the first holder component 702 has been adapted specifically to locate an annuloplasty prosthesis which takes the form of a band having two ends 705, rather than a closed ring prosthesis as illustrated in conjunction with the embodiment of FIGS. 24–25, discussed above. In this case, a suture 707 is provided, which is employed to pull the ends 505 of the band toward one another, assisting in retaining it on the first component 702. The mechanism by which the prosthesis 704 is maintained on the first holder component 702 is illustrated in more detail in FIGS. 27 and 28.

Figure 27:
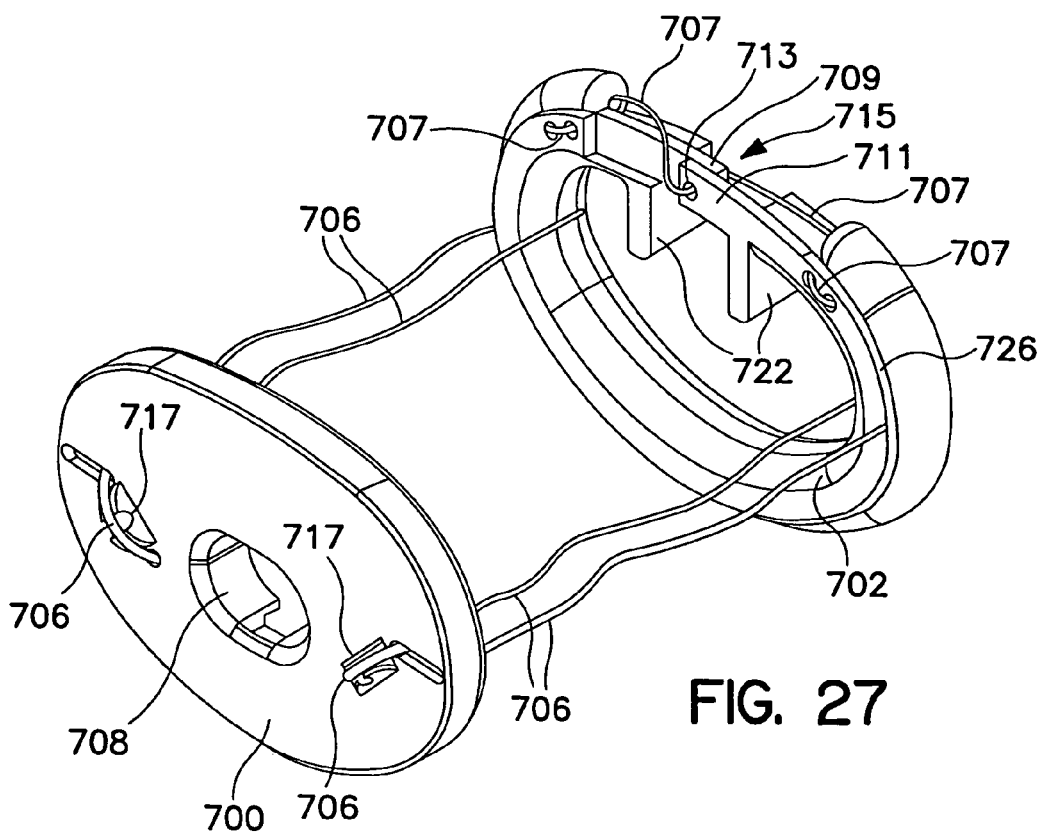
FIG. 27 illustrates the embodiment of FIG. 26 with the first and second components separated from one another.

FIG. 27 illustrates the holder of FIG. 26 with the second holder component 700 moved upward away from the first holder component 702. All numbered elements correspond to those in FIG. 28. In this view, it can be seen that the first holder component 702 is provided with a radially extending upper flange 726, extending outwardly along the upper surface of prosthesis 704. Not visible in this view are a series of outwardly extending projections located along the lower edge of first holder component 702 and lying along side the lower surface of the prosthesis 704. The prosthesis 704 is maintained between the upper flange and the lower projections by means of suture 707. Suture 707 is anchored to the first component adjacent the ends of the prosthesis 704, entering the prosthesis through its inner surface, exiting through its end surfaces and passing through cutting mechanism 715, located between the ends 705 of the prosthesis 704.

Like the first component 602 illustrated in the embodiment of FIGS. 24 and 25 discussed above, the first component 702 takes the form of an open ring, having inwardly directed projections 722. Although not illustrated in FIGS. 26–28, it should be understood that while the first and second holder components 702, 700 are located adjacent one another, a rectangular projection from second component 700 corresponding to projection 510 (FIG. 21) is located between the projections 722, preventing cutting of suture 707 and release of the prosthesis prior to upward movement of the second component. After upward movement of the second component 700, projections 722 may be squeezed toward one another to reduce the circumference of the first component. Cutter 715 cuts suture 707 upon movement of projections 722 toward one another.

The cutter takes the form of two rectangular projections 709 and 711 extending from the first component 702 adjacent the inwardly extending projections 722 and overlapping one another such that they slide relative to one another upon movement of projections 722 toward one another. Each of the projections 709 and 711 is provided with a hole, of which only one, 713, is visible in this view. In the normal position the holes are aligned with one another, allowing for passage of suture 707 through the holes. Upon movement of the projections 722 closer to one another, projections 709 and 711 slide relative to one another, causing relative movements of the corresponding holes on the members, cutting suture 707, releasing prosthesis 704 from the first holder component 702. The suture, after cutting, remains attached to the first holder component.

Figure 28:
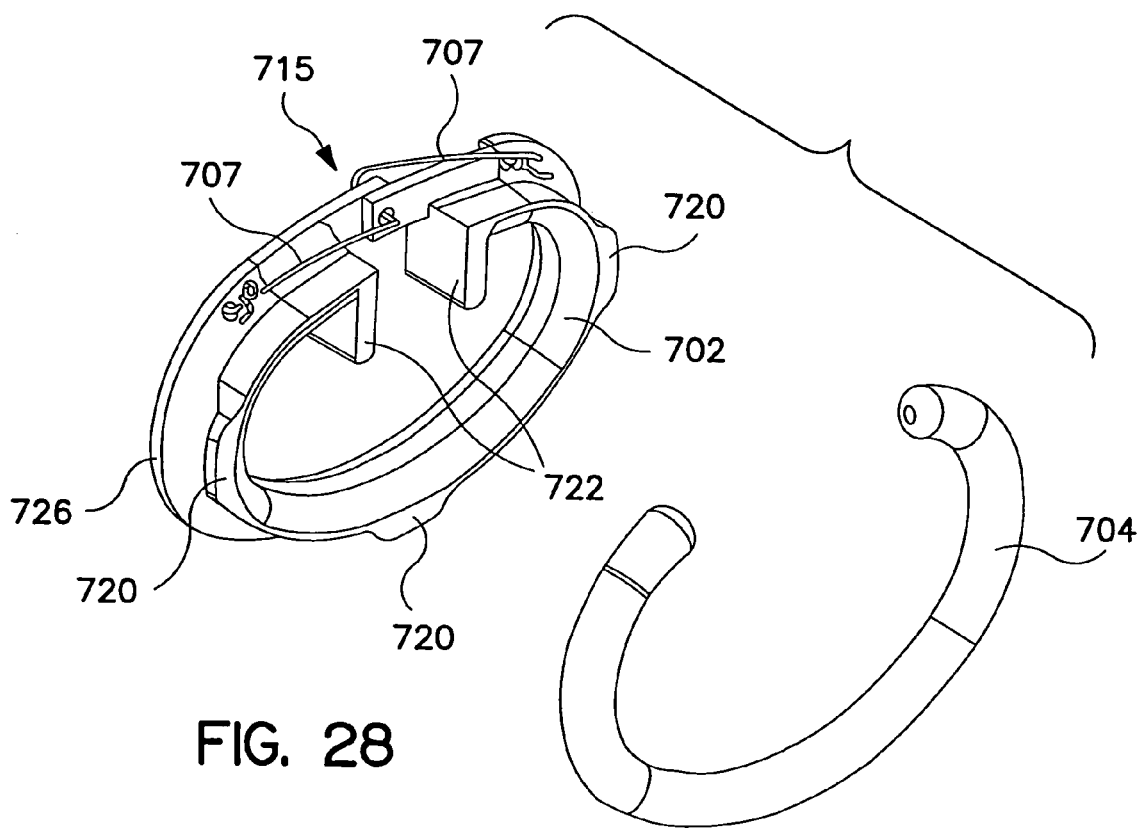
FIG. 28 illustrates the first component of the embodiment of FIG. 26, with the annuloplasty prosthesis removed in order to illustrate further details of construction of the first component.

FIG. 28 is a perspective drawing of the first holder component 702 with the prosthesis 704, shown removed from the holder. All numbered components correspond to those illustrated in FIGS. 26 and 27. In this view, the configuration of the radially extending projections 720, normally located adjacent the lower surface of the prosthesis 704 can be seen. Suture 707 is shown intact to better illustrate its routing prior to cutting. The embodiment as illustrated is probably most desirably used with an inextensible annuloplasty band as described above. However, it may also be of use with a somewhat extensible band. It is also believed that the cutter mechanism as disclosed or modified might in some cases be useful in a holder for an annuloplasty ring, maintained to the holder by means of sutures passing through or around the prosthesis.

We claim:
1. An annuloplasty system, comprising:
a first holder component having an upper surface, a lower surface and a circumferential surface corresponding generally to the configuration of a heart valve annulus, the first holder component further comprising at least one outwardly extending member and the first holder component being deformable from a mount configuration to a reduced circumference configuration;
an annuloplasty prosthesis, located adjacent to and extending at least partially around the circumferential surface of the first holder component in the mount configuration such that the outwardly extending member extends alongside a lower surface of the prosthesis, preventing the prosthesis from moving downward and off of the first holder component;
a second holder component, coupled to and extending above the first holder component, movable upwardly relative to the first holder component and comprising means for preventing deformation of the first holder component to the reduced circumference configuration until movement of the second holder component relative to the first holder component; and
wherein the second holder component is releasably secured adjacent to the first holder component by cuttable sutures.
2. A system as in claim 1 wherein the first holder component is an open ring with spaced ends and wherein the second holder component comprises a projection locatable between the spaced ends to prevent movement of the spaced ends toward one another and reduction of the circumference of the first holder component.

3. A system as in claim 2, wherein the projection extends downwardly from the second holder component and exits its location between the spaced ends upon upward movement of the second holder component.

4. A system as in claim 1 wherein the at least one outwardly extending projection comprises a series of spaced projections, located along the circumferential surface.

5. A system as in claim 1 wherein the at least one outwardly extending projection comprises a single elongated projection, extending along the circumferential surface.

6. A system as in claim 1 wherein the at least one outwardly extending projection comprises a lower edge of a groove extending along the circumferential surface.

7. An annuloplasty system, comprising:
a first holder component having an upper surface, a lower surface and a circumferential surface corresponding generally to the configuration of a heart valve annulus, the first holder component comprising at least one outwardly extending member; and a suture cutter comprising a cutter element on the first holder component that is movable relative to another element of the first holder component;
an annuloplasty prosthesis, located adjacent to and extending at least partially around the circumferential surface such that the outwardly extending member extends alongside a lower surface of the prosthesis, preventing the prosthesis from moving downward and off of first holder component; and
a cuttable suture, holding the annuloplasty prosthesis adjacent the circumferential surface and passing through the suture cutter.

8. A system as in claim 7 wherein the first holder component is deformable to display a reduced circumference.

9. A system as in claim 8 wherein the cutter element is movable relative to the other element for cutting the suture responsive to deformation of the first holder component.

10. A system as in claim 9 wherein the first holder component is an open ring having spaced ends and wherein the cutter is coupled to the spaced ends and comprises means for cutting the suture responsive movement of the spaced ends toward one another.

11. A system as in claim 10, further comprising a second holder component, coupled to and extending above the first holder component, movable upwardly relative to the first holder component and comprising means for preventing movement of the spaced ends toward one another until upward movement of the second holder component.

12. A system as in claim 11 wherein the second holder component comprises a projection locatable between the spaced ends to prevent movement of the spaced ends toward one another and reduction of the circumference of the first holder component.

13. A system as in claim 7, further comprising a second holder component, coupled to and extending above the first holder component, movable upwardly relative to the first holder component and comprising means for preventing deformation of the first holder component until upward movement of the second holder component.

14. An annuloplasty system, comprising:
a first holder component having an upper surface, a lower surface and a circumferential surface corresponding generally to the configuration of a heart valve annulus, the first holder component being an open ring comprising an arcuate element extending from a first end to a second end, the first and second ends being spaced from one another and movable toward one another to reduce the ring's circumference and comprising at least one outwardly extending member; and
an annuloplasty prosthesis, located adjacent to and extending at least partially around the circumferential surface such that the outwardly extending member extends alongside a lower surface of the prosthesis.

15. A system as in claim 14, wherein the first holder component comprises engaging means located at the ends of the spaced ring ends for facilitating movement of the spaced ends toward one another.

16. A system as in claim 15, wherein the engaging means comprises projections extending interiorly of the open ring.

17. A system as in claim 14, further comprising a second holder component, coupled to and extending above the first holder component, movable upwardly relative to the first holder component and comprising means for preventing movement of the spaced ends toward one another holder component until upward movement of the second holder component.

18. A system as in claim 17 wherein the second holder component comprises a projection locatable between the spaced ends to prevent movement of the spaced ends toward one another and reduction of the circumference of the first holder component.

19. A system as in claim 18, wherein the projection extends downwardly from the second holder component and exits its location between the spaced ends upon upward movement of the second holder component.

* * * * *